(12) United States Patent
Bommarito et al.

(10) Patent No.: US 10,563,245 B2
(45) Date of Patent: Feb. 18, 2020

(54) WASH MONITOR AND METHOD OF USE

(71) Applicant: 3M INNOVATIVE PROPERTIES COMPANY, St. Paul, MN (US)

(72) Inventors: G. Marco Bommarito, Stillwater, MN (US); Ting Liu, Shanghai (CN); Timothy J. Nies, Stillwater, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 60 days.

(21) Appl. No.: 14/432,807

(22) PCT Filed: Oct. 1, 2013

(86) PCT No.: PCT/US2013/062782
§ 371 (c)(1),
(2) Date: Apr. 1, 2015

(87) PCT Pub. No.: WO2014/058652
PCT Pub. Date: Apr. 17, 2014

(65) Prior Publication Data
US 2015/0257844 A1 Sep. 17, 2015

Related U.S. Application Data

(60) Provisional application No. 61/710,829, filed on Oct. 8, 2012, provisional application No. 61/773,854, filed on Mar. 7, 2013.

(51) Int. Cl.
*C12Q 1/66* (2006.01)
*A61L 2/28* (2006.01)
(Continued)

(52) U.S. Cl.
CPC ............... *C12Q 1/66* (2013.01); *A61B 90/70* (2016.02); *A61L 2/28* (2013.01); *C12Q 1/22* (2013.01);
(Continued)

(58) Field of Classification Search
CPC .. C12Q 1/66; C12Q 1/22; A61B 90/70; A61B 2090/702; A61L 2/28;
(Continued)

(56) References Cited

U.S. PATENT DOCUMENTS

| 4,978,504 A | 12/1990 | Nason |
| 5,073,488 A | 12/1991 | Matner et al. |

(Continued)

FOREIGN PATENT DOCUMENTS

| CN | 1799491 A | 7/2006 |
| CN | 101539554 A | 9/2009 |

(Continued)

OTHER PUBLICATIONS

Brochure entitled "WASH-CHECKS® Disposable Wash Monitors & Reusable Holders for Monitoring the Wash Process in Washer-Disinfectors" from SteriTec 1 pg. (date unknown but believed to be prior to the date of the filing of the present application).

(Continued)

*Primary Examiner* — Dennis White
(74) *Attorney, Agent, or Firm* — 3M Innovative Properties Company; Trisha D. Adamson

(57) ABSTRACT

The present disclosure provides a monitoring device comprising a test composition, a test element comprising a test portion to which the test composition is releasably adhered, a detection reagent, and a container comprising a first end with an opening and a second end opposite the first end. The test composition comprises a predetermined quantity of tracer analyte. The container is configured to receive the test portion and configured to be operationally coupled to an analytical instrument. The tracer analyte and the detection reagent each are capable of participating in one or more chemical reaction that results in the formation of a detect- (Continued)

able product. A method of using the monitoring device to assess the efficacy of a washing process is also provided.

21 Claims, 8 Drawing Sheets

(51) Int. Cl.
*C12Q 1/22* (2006.01)
*A61B 90/70* (2016.01)

(52) U.S. Cl.
CPC . *A61B 2090/702* (2016.02); *C12Y 113/12007* (2013.01); *G01N 2333/90241* (2013.01); *Y10T 436/13* (2015.01)

(58) Field of Classification Search
CPC .. G01N 2333/90241; C12Y 113/12007; Y10T 436/13
See application file for complete search history.

(56) References Cited

U.S. PATENT DOCUMENTS

| | | | |
|---|---|---|---|
| 5,266,266 A | 11/1993 | Nason | |
| 5,477,794 A | 12/1995 | Klundt | |
| 5,538,629 A | 7/1996 | Blaney et al. | |
| 5,736,355 A * | 4/1998 | Dyke | C12Q 1/18 435/287.4 |
| 5,879,635 A | 3/1999 | Nason | |
| 6,083,755 A | 7/2000 | Buess et al. | |
| 6,107,097 A | 8/2000 | Pfeifer | |
| 6,395,551 B1 | 5/2002 | Kipke et al. | |
| 6,447,990 B1 | 9/2002 | Alfa | |
| 2001/0026942 A1* | 10/2001 | Carpenter | A61B 10/0096 436/86 |
| 2003/0164182 A1 | 9/2003 | Jacobs et al. | |
| 2005/0221471 A1 | 10/2005 | Ramsay et al. | |
| 2006/0216196 A1 | 9/2006 | Satoh et al. | |
| 2006/0218944 A1 | 10/2006 | He et al. | |
| 2006/0219261 A1 | 10/2006 | Lin et al. | |
| 2007/0074742 A1 | 4/2007 | Lin et al. | |
| 2007/0249054 A1 | 10/2007 | Doi et al. | |
| 2008/0193631 A1 | 8/2008 | Kanamori et al. | |
| 2008/0206740 A1* | 8/2008 | Skiffington | B01L 3/5029 435/5 |
| 2009/0220378 A1 | 9/2009 | McDonnell et al. | |
| 2010/0190171 A1 | 7/2010 | Kshirsagar et al. | |
| 2011/0146419 A1 | 6/2011 | Gonzalez | |
| 2011/0182770 A1 | 7/2011 | Chandrapati et al. | |
| 2011/0200992 A1 | 8/2011 | Chandrapati et al. | |
| 2012/0009588 A1 | 1/2012 | Rajagopal et al. | |
| 2013/0244225 A1 | 9/2013 | Kshirsagar | |

FOREIGN PATENT DOCUMENTS

| | | |
|---|---|---|
| DE | 44 37 103 | 4/1996 |
| DE | 196 49 925 | 6/1998 |
| DE | 20 2007 017 612 U | 3/2008 |
| EP | 1 769 808 | 4/2007 |
| GB | 1 344 140 | 1/1974 |
| JP | 6-088788 | 3/1994 |
| JP | 2006-346136 | 12/2006 |
| JP | 2007-244702 | 9/2007 |
| JP | 2009-039192 | 2/2009 |
| JP | 2009-061012 | 3/2009 |
| WO | WO 1993/00994 | 1/1993 |
| WO | WO 1996/18580 | 6/1996 |
| WO | WO 1998/16260 | 4/1998 |
| WO | WO 1998/40736 | 9/1998 |
| WO | WO 2000/09743 | 2/2000 |
| WO | WO 2009/085357 | 7/2009 |
| WO | WO 2009/134509 | 11/2009 |
| WO | WO 2012/078426 | 6/2012 |
| WO | WO 2012/112482 | 8/2012 |

OTHER PUBLICATIONS

Web information on wash monitors from SteriTec entitled Sterility Assurance, Cleaning Assurance, SteriTec Assurance; 13 pgs. (date unknown but believed to be prior to the date of the filing of the present application).
Product Brochure entitled "Preventative Maintenance & Thermal Validation Testing for your DEKO Washer Disinfector" from Rhima Australia Pty Ltd.; 2 pgs. (date unknown but believed to be prior to the date of the filing of the present application).
Simpson, W.J. et al.; "Repeatability of hygiene test systems in measurement of low levels of ATP"; Report 30606 from Cara Technology Limited; 2006; 2 pgs.
Simpson, W.J. et al.; "Protocol for assessing the sensitivity of hygiene test systems for live microorganisms and food residues"; Report 120906 from Cara Technology Limited; 2006; 2 pgs.
Brochure entitled "3M™ Clean-Trace™ ATP Hygiene Monitoring Products—3M Food Safety"; 2010; 13 pgs.

* cited by examiner

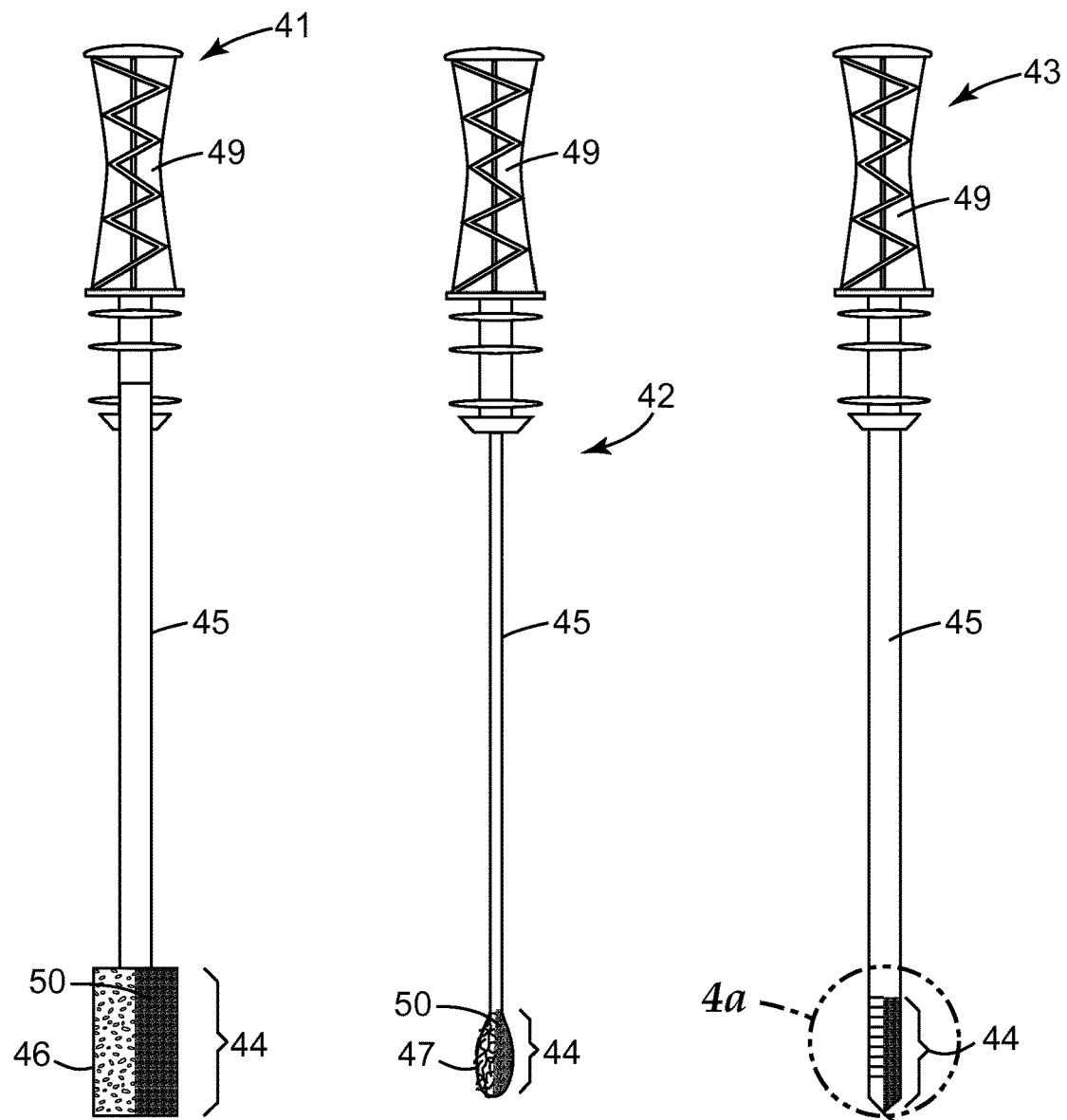
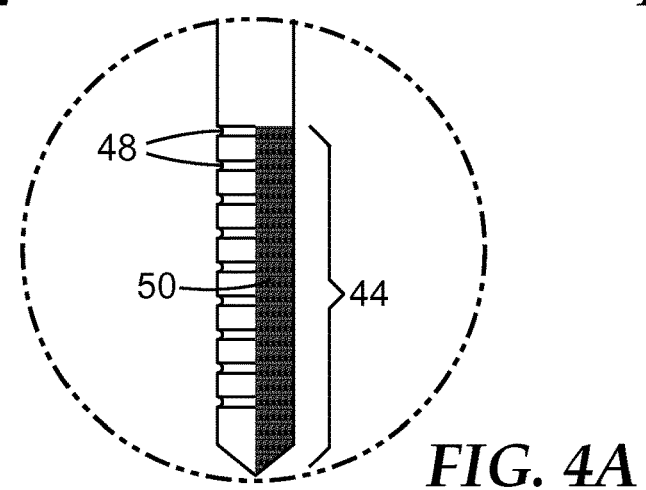
FIG. 2  FIG. 3  FIG. 4
FIG. 4A

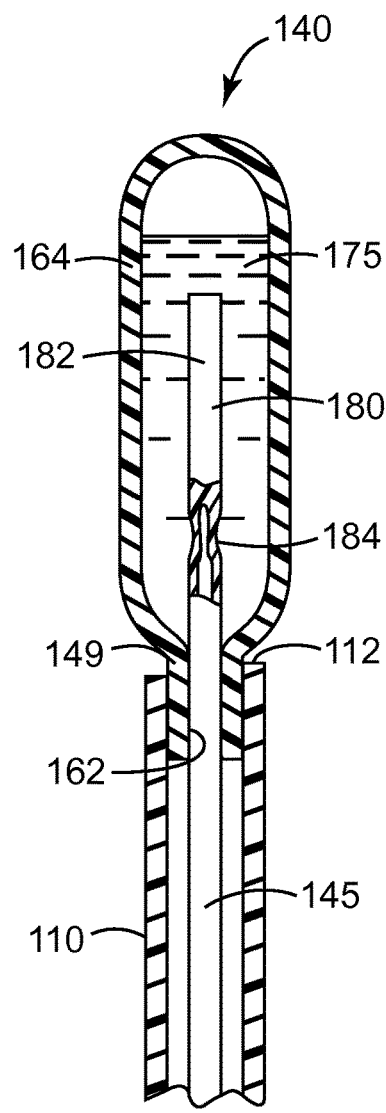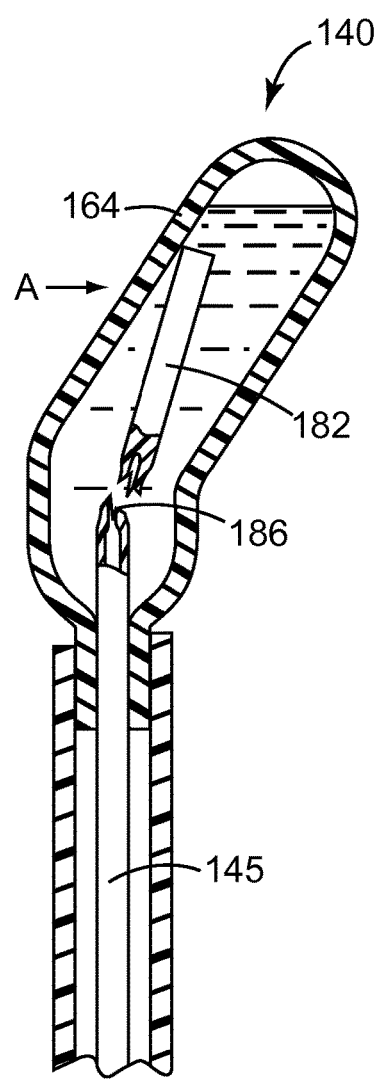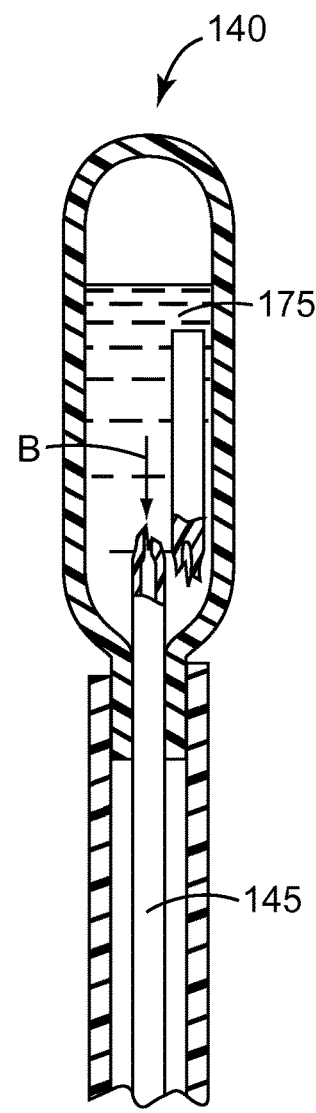
*FIG. 5A*  *FIG. 5B*  *FIG. 5C*

WASH MONITOR AND METHOD OF USE

CROSS-REFERENCE TO RELATED APPLICATION

This application is a national stage filing under 35 U.S.C. 371 of PCT/US2013/062782, filed Oct. 1, 2013, which claims priority to U.S. Provisional Patent Application Nos. 61/710,829, filed on Oct. 8, 2012 and 61/773,854, filed Mar. 7, 2013, the disclosure of which are incorporated by reference in their entirety herein.

BACKGROUND

Hospitals and clinics frequently rely on washing equipment and processes to remove biological soil from reusable medical instruments and devices. In addition, the solvent used in the washing processes may contain chemical and/or enzymes to facilitate the removal and/or disinfection of the biological soil. In operation, the washing equipment can fail to adequately clean the instruments and devices due to one or more of a variety of reasons including, for example, washing the objects at an unacceptably low temperature and providing an inadequate volume and/or velocity of solvent to the washing process. In addition, the wash solvent can fail to adequately clean the instruments and devices due to one or more of a variety of reasons including, for example, loss of chemical and/or enzyme activity due to aging and improper dilution of active ingredients (e.g., chemicals or enzymes) in the wash solvent.

Disposable wash monitors are used for monitoring the efficacy of wash processes in washer-disinfector equipment, for example. A wash monitor typically includes a test soil disposed on a surface of an object that is placed into a washing machine. The test soil may comprise biological molecules such as, for example, human or animal red blood cells, protein, and fat. The monitor also includes a detectable marker (e.g., a pigment or dye) that can be observed to determine whether the washing machine meets minimum requirements for impinging a wash solution against an object and/or to determine whether the wash solution meets minimum requirements for chemical and/or enzymatic treatment of the object to be cleaned.

Although a variety of wash monitors are available to assess the efficacy of a washing process, there remains a need for improved wash monitors.

SUMMARY

The present disclosure generally relates to an article to assess the efficacy of a washing process and a method of use thereof. The inventive article is a modification of an existing article that is typically used to detect a chemical analyte in a sample. The existing article includes a sample acquisition device (e.g., a swab) to obtain a sample with an unknown quantity of the chemical analyte. The inventive article deliberately adulterates the sample acquisition device such that it comprises a predetermined amount of the chemical analyte releasably adhered thereto, thus destroying its utility for its originally-intended purpose. In the inventive method, the operator exposes the adulterated sample acquisition device (hereinafter, "test element") to a washing process and subsequently measures the quantity of chemical analyte (hereinafter, "tracer analyte"), if any, remaining on the test element. In addition, the present disclosure provides a test element with a composition comprising the tracer analyte releasably adhered thereto and a system for assessing the efficacy of a washing process.

In one aspect, the present disclosure provides a monitoring device. The monitoring device can comprise a test composition comprising a predetermined quantity of tracer analyte, a test element comprising a test portion to which the test composition is releasably adhered, a detection reagent, and a container comprising a first end with an opening and a second end opposite the first end. The container is configured to receive the test portion and configured to be operationally coupled to an analytical instrument. The tracer analyte and the detection reagent each are capable of participating in one or more chemical reaction that results in the formation of a detectable product. In any embodiment, the test portion can comprise at least one recessed area, wherein the test composition is adhered in the recessed area. In any of the above embodiments, the test composition further can comprise a polymeric binder. In any of the above embodiments, the tracer analyte can be selected from the group consisting of a plurality of viable microorganisms or a biomolecule associated therewith, an acid, a base, a nucleotide, a protein, a nucleic acid, a carbohydrate, or hemoglobin. In any of the above embodiments, the test portion can comprise a porous fibrous nonwoven matrix, wherein the plurality of viable microorganisms is disposed on or in the fibrous nonwoven matrix.

In any of the above embodiments, the monitoring device further can comprise a frangible seal, wherein a receiving chamber is disposed on a first side of the frangible seal proximate the opening and a cuvette chamber is disposed on a second side of the frangible seal distal the opening. In any of the above embodiments, container can include a first solvent disposed therein. In any of the above embodiments, the test element further can comprise a reservoir with a second solvent disposed therein, a hollow stem, and a liquid flow regulator capable of placing the reservoir in fluid communication with the hollow stem. In any of the above embodiments, the monitoring device further can comprise a secural element.

In another aspect, the present disclosure provides a method of assessing the efficacy of a washing process. The method can comprise exposing the test portion of a monitoring device according to any one of the above embodiments to the washing process; after exposing the test portion to the washing process, contacting the test portion with the detection reagent in the container; and using the analytical instrument to detect a presence or an absence of the detectable product, wherein the presence of the detectable product indicates a presence of tracer analyte on the test portion after exposing the test portion to the washing process. In any embodiment of the method, exposing the test portion to the washing process can comprise placing the test portion into an automated washer and performing at least a portion of an automated wash cycle while the test portion is disposed in the automated washer. In any of the above embodiments of the method, using the analytical instrument to detect a presence or an absence of the detectable product can comprise using the analytical instrument to measure a quantity of the tracer analyte. In any of the above embodiments of the method, exposing the test portion of a monitoring device can comprise exposing the test portion of a plurality of monitoring devices, wherein the method further can comprise positioning a first monitoring device at a first predefined location in the automated washer and positioning a second monitoring device at a second predefined location in the automated washer. In any of the above embodiments, the method further can comprise comparing at least one measured quantity of the tracer analyte to a predefined standard.

In any of the above embodiments, the method further can comprise associating a first datum related to a quantity of tracer analyte detected in a sample with a second datum related to other information related to the sample and electronically storing the associated first and second data. In some embodiments, the second datum can comprise information selected from the group consisting of a date, a time, a washing apparatus, an operator, an instrument to be washed, and a combination of two or more of any of the foregoing test data. In any of the above embodiments, the method further can comprise the step of placing the test portion of the monitoring device in a receiver configured to restrict fluidic accessibility to the test portion. In any of the above embodiments of the method, placing the test portion of the monitoring device in a receiver configured to restrict fluidic accessibility to the test portion can comprise placing the test portion into an interior space of a lumened object.

In yet another aspect, the present disclosure provides a method of processing an object to be decontaminated. The method can comprise processing as a single batch in a decontamination process an object having an unknown amount of biological soil disposed thereon and/or therein and a monitoring device comprising container, a test portion that includes a predetermined quantity of tracer analyte, and a detection reagent according to any of the above embodiments; after exposing the test portion to the decontamination process, contacting the test portion with the detection reagent in the container; and using an analytical instrument to detect a presence or an absence of the detectable product, wherein the presence of the detectable product indicates a presence of the tracer analyte on the test portion after exposing the test portion to the washing process. In any embodiment, processing as a single batch in a decontamination process the object and the monitoring device can comprise processing as a single batch in a decontamination process the object and a plurality of the monitoring devices. In any embodiment, processing a plurality of monitoring devices comprises processing a first device at a first location in an automated washer or the automated washer-disinfector and processing a second device at a second location in the automated washer or the automated washer-disinfector.

In yet another aspect, the present disclosure provides a kit. The kit can comprise a container comprising a first end with an opening and a second end opposite the first end and a test element comprising a test portion to which a test composition is releasably adhered. The container can include a detection reagent disposed therein. The test composition comprises a predetermined quantity of tracer analyte. The container is configured to receive the test portion and configured to be operationally coupled to an analytical instrument. The tracer analyte and the detection reagent each are capable of participating in one or more chemical reaction that results in the formation of a detectable product. In any embodiment of the kit, the test element further can comprise a reservoir with a solvent disposed therein, wherein the reservoir comprises test element comprises a hollow stem and the reservoir comprises a liquid flow regulator capable of placing the reservoir in fluid communication with the hollow stem. In any of the above embodiments, the kit further can comprise a means to secure a test element. In any of the above embodiments, the kit further can comprise an article comprising a receiver, the article configured to restrict fluidic accessibility to the test portion. In some embodiments, the article can be a lumened object.

In yet another aspect, the present disclosure provides a system. The system can comprise a monitoring device comprising a test element that includes a test portion to which a test composition comprising a predetermined quantity of a tracer analyte is releasably adhered according to any one of the above embodiments and an analytical instrument capable of detecting the detectable product. The container is configured to receive the test portion and configured to be operationally coupled to the analytical instrument. In any embodiment, the system further can comprise a computer capable of receiving data from the analytical instrument and a memory capable of storing the received data.

In yet another aspect, the present disclosure provides an article. The article can comprise a homogeneous dried composition removably adhered thereto, wherein the composition comprises a predetermined amount of adenosine-5'-triphosphate. In any embodiment of the article, the composition further can comprise a dye in an amount sufficient to be optically detectable. In any of the above embodiments of the article, the composition further can comprise a polymeric binder.

In yet another aspect, the present disclosure provides a homogeneous, dried artificial test soil consisting essentially of adenosine-5'-triphosphate, or a salt thereof, and a polymeric binder. In any embodiment of the test soil, the polymeric binder can comprise polyvinyl alcohol, polyethylene glycol, or mixtures thereof.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, "a" test element can be interpreted to mean "one or more" test elements.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

BRIEF DESCRIPTION OF DRAWINGS

FIG. 2 is a side view of a test element, partially in section, having an alternative test portion comprising a foam material.

FIG. 3 is a side view of a test element, partially in section, having an alternative test portion comprising a fibrous material.

FIG. 4 is a side view of a test element, partially in section, having an alternative test portion comprising a plurality of recessed areas.

FIG. 4A is a detail view of the test portion of the test element of FIG. 4.

FIG. 5A-C are side views, partially in section, of a portion of one embodiment of an alternative test element comprising a hollow stem, a deformable reservoir, and a breakable valve that places the reservoir in selective fluid communication with the stem, showing how deformation of the reservoir causes breakage of the valve permitting the flow of a liquid into the stem.

DETAILED DESCRIPTION

Figure 1:
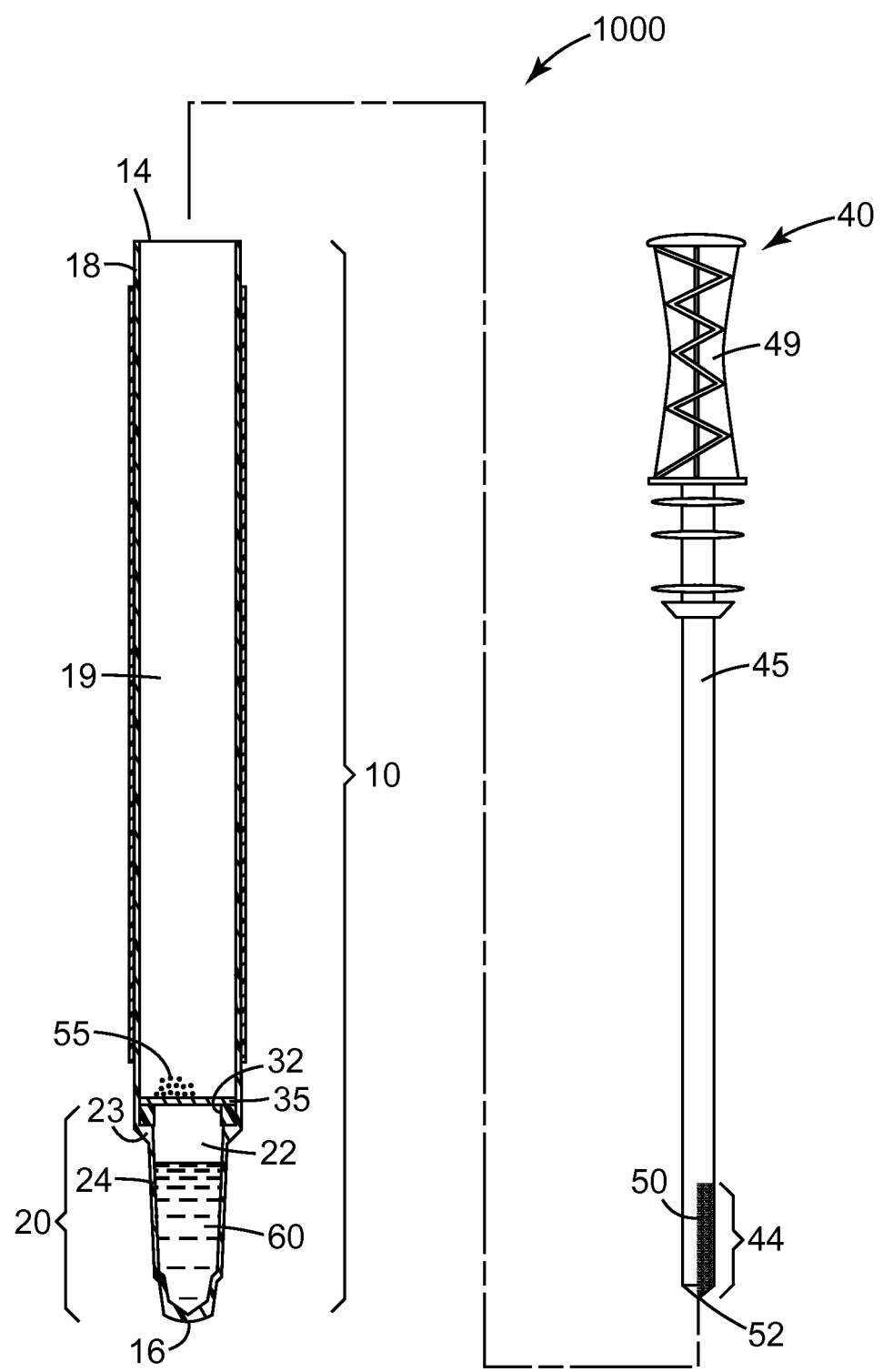
FIG. 1 is an exploded view of one embodiment of a monitoring device comprising a unitary container, shown in cross-section, and a test element according to the present disclosure.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure relates to a process equipment monitoring device and a method of use thereof. The process equipment monitoring device can be used to test the efficacy of a washing process and, in particular, a washing process conducted by an automated washer. The monitoring device is an adaptation of any one of a variety of existing test devices that are currently used to detect the presence or quantity of a chemical analyte. Each of the existing monitoring devices comprises a sample acquisition device (e.g., a swab or dipstick) that is configured for contact with a liquid or solid sample such that the sample acquisition device retains at least a portion of the sample. The sample acquisition device is subsequently inserted into a container where it contacts a detection reagent that reacts directly or indirectly with the analyte to form a detectable product (i.e., a colored compound) that can be observed, and optionally quantitated, by visible inspection or by using an analytical instrument (e.g., a spectrophotometer or luminometer).

The inventive process equipment monitor includes a test element, which is analogous to the sample acquisition device described above, but has been modified in a way that renders it substantially unsuitable for its original purpose (i.e., to detect unknown quantities of analyte). The modification includes deliberately adulterating the test element with a predetermined quantity of tracer analyte that the existing test device was designed to detect. Furthermore, tracer analyte is applied to the test element in such a way that a portion or all of the tracer analyte is released from the test element when the test element is exposed to a washing process that meets or exceeds predefined standards for efficacy.

The above-mentioned existing test devices are used to detect the presence, absence, or quantity of a variety of analytes including, for example, biological analytes such as carbohydrates (e.g., glucose), protein, nucleic acid, and hemoglobin. Typically, the test devices include a sample-acquisition component (e.g., a swab, a pipette, a sponge, or the like) to obtain a sample to be tested and a container into which the sample acquisition device and/or sample can be placed in order to detect the analyte. The container may include a detection reagent disposed therein, the detection reagent capable of interacting with the analyte to form a detectable moiety (e.g., a chemical derivative of the analyte or a detectable byproduct of the interaction such as light, for example). In addition, many of the test devices are adapted to be used with an analytical instrument to obtain the result of the test. For example, the container of the test device may be shaped and dimensioned so that at least a portion of the container can be inserted into the analytical instrument and the result is automatically read, and optionally exported and/or electronically saved, by the instrument.

Nonlimiting examples of such existing test devices include the 3M CLEAN-TRACE Surface ATP Swab available from 3M Company (St. Paul, Minn.), the AQUASNAP ATP Water Test available from Hygiena (Camarillo, Calif.), the ACCUPOINT 2 ATP Sanitation Monitoring System available from Neogen Corporation (Lansing, Mich.), and the PRO-CLEAN Rapid Protein Residue Test available from Hygiena.

The inventive monitoring devices of the present disclosure embody at least one modification of these test devices. The monitoring devices are modified such that the sample acquisition component of the original test device (hereinafter, called the "test element" of the modified monitoring device) is adulterated with a test composition that comprises a predetermined quantity of the tracer analyte the test device is designed to detect. In contrast to a typical prior art test device, which is configured to detect the absence, presence, or quantity of a particular analyte; the modified test device (i.e., the monitoring device) is configured to detect whether the test element has been exposed to an environment that diminished or eliminated the tracer analyte-containing test composition imbued thereon.

In one aspect, the present disclosure provides a monitoring device. The monitoring device can be used in a variety of methods disclosed herein. FIG. 1 shows an exploded view of one embodiment of a monitoring device 100 according to the present disclosure. The monitoring device 100 comprises a container 10 and a test element 40. The test element 40 comprises a test portion 44, to which a test composition 50 is releasably adhered, and a handle 49. The container 10 has a first end 12 and a second end 16 opposite the first end. The first end 12 of container 10 comprises opening 14 into which at least a portion of a test element 40 can be inserted.

The container 10 can be formed (e.g., by injection molding or extrusion) of polymeric materials (e.g., polyethylene, polypropylene) as a unitary part. As with the existing test devices described herein, when detection of the tracer analyte comprises optical detection of a product derived therefrom, the container 10 should be formed using materials and processes that permit the transmission of wavelengths of light that are suitable to permit optical detection of the product.

Optionally, the monitoring device 100 further may comprise a frangible seal 35 disposed in the container 10. The frangible seal 35, if present can partition the container 10 into two chambers, a receiving chamber 19 proximate the opening 14 and a cuvette chamber 22 distal the opening 14. The frangible seal 35 can be made from a water-resistant material such as, for example, a plastic film, a metal foil, or a metal-coated plastic film. The frangible seal 35 can be coupled to the container 10 via coupling means that are known in the art (e.g., an adhesive, an ultrasonic weld, and the like). The frangible seal 35 may be directly coupled (not shown) to the container 10 at a structure such as flange 23, for example. Alternatively, the frangible seal 35 can be coupled (e.g., via an adhesive, an ultrasonic weld, or the like) to a separate structure (e.g., sealing member 32), which can be inserted into the container 10 and disposed against flange 23, as shown in FIG. 1. The sealing member 32 can be formed from a relatively flexible and/or malleable material such as, for example, polyethylene, polypropylene, silicone, or butyl rubber. Preferably, the frangible seal 35 and sealing member 32, if present, form a liquid-resistant barrier between the receiving chamber 19 and the cuvette chamber 22.

The container 10 can be formed (e.g., by injection molding or extrusion) of polymeric materials (e.g., polyethylene, polypropylene, polystyrene, polycarbonate). The walls of the cuvette portion 20 can be molded, for example, to form one of a variety of geometric shapes such as, for example, cubic, cuboid, cylindrical, conical, frusto-conical, other geometric shapes suitable to be operationally coupled to an analytical instrument (not shown). Preferably, the wall 24 of the cuvette portion 20 can be configured (e.g., by using a relatively transparent or translucent material and/or by constructing the cuvette portion with at least one relatively thin wall 24) to permit the transmission of light (e.g., visible light) into and/or out of the cuvette portion.

An optional lamina 70 can be affixed (e.g., adhesively affixed) to the container (e.g., proximate the opening). The lamina 70 can be made from paper or a plastic film, for example, and may be used as a label.

The monitoring device further comprises a detection reagent 55 disposed in the container. In the illustrated embodiment, the detection reagent 55 is disposed in the container as a solid (e.g., a solid powder). In any embodiment, the detection reagent may be dissolved or suspended in a solvent as described below. In some embodiments (not shown), the monitoring device may comprise a second frangible seal disposed between the first frangible seal and the opening. The space between the first and second frangible seals forms a compartment in which the reagent, either in dry (e.g., powder) or liquid form, can be disposed.

Optionally, in any embodiment, the container can include a solvent disposed therein. In the illustrated embodiment, the first solvent 60 is disposed in the cuvette chamber 22. In any embodiment (not shown), the solvent alternatively or additionally may be disposed in the receiving chamber 19. In any embodiment, the frangible seal 35 can prevent unintended movement of the first solvent 60 between the receiving chamber 15 and the cuvette chamber 22.

In any embodiment, the first solvent 60 can be a liquid in which a portion (e.g., the tracer analyte) or all of the test composition 50 is soluble. In any embodiment, the first solvent 60 may comprise water. In some embodiments, the first solvent 60 additionally comprises a buffer component to maintain the solvent within a predefined pH range (e.g., a pH range that is suitable for a reaction used in the detection of the tracer analyte). In some embodiments, the solvent may comprise a surfactant (e.g., a nonionic surfactant) to facilitate the dispersion of the tracer analyte and/or test composition 50 into the first solvent 60. A suitable surfactant does not substantially interfere with a reaction, a detection reagent, and/or an instrument that is used for the detection of the tracer analyte.

A monitoring device of the present disclosure comprises a detection reagent for detecting the tracer analyte. In some embodiments, the monitoring device may comprise a plurality of detection reagents. At least one detection reagent may be disposed in the container. In any embodiment, at least one detection reagent may be disposed in a sealed chamber (e.g., the cuvette chamber) of the container. In any embodiment, the at least one detection reagent may be dissolved in the solvent. In some embodiments, (not shown) the detection reagent may be disposed on (e.g., as a coating such as a dried coating) and/or in the test element (e.g., dissolved in a solvent disposed in a reservoir, as disclosed herein). The particular detection reagent disposed in the monitoring device is selected according to the tracer analyte and/or the instrument that is used to detect the tracer analyte, the derivative of the tracer analyte, or the byproduct of the tracer analyte. A person having ordinary skill in the art will recognize a suitable detection reagent for a particular tracer analyte. By way of example, suitable detection reagents to detect a protein tracer analyte include a $Cu^{2+}$ compound (e.g., $CuSO_4$), sodium tartrate, sodium carbonate, sodium bicarbonate, and bicinchoninic acid. One or more of the foregoing reagents can be provided in a container according to the present disclosure. By way of another example, suitable detection reagents to detect ATP tracer analyte include luciferin and luciferase. In any embodiment, a first detection reagent may be provided in one chamber of the container and a second detection reagent may be provided in another chamber of the container.

In some embodiments, the solvent may comprise a stabilizer (e.g. enzyme stabilizers).

Referring back to FIG. 1, the test element 40 comprises a test portion 44 and an optional stem 45. The stem 45 can be constructed from a variety of materials, such as wood, plastic, metal, or combinations thereof. In some embodiments, the stem 45 can be fabricated from a sufficiently flexible material (e.g., metal wire or plastic polymer) to insert the test portion 44 into tortuous spaces. Advantageously, in those embodiments, the test element can be used to assess the ability of a washing process to penetrate effectively into the tortuous spaces. In other embodiments, the stem 45 can be relatively inflexible. The stem 45 is adapted to be coupled (e.g., by friction fit or via an adhesive) to the handle 49. In use, the stem 45 or the handle 49 can be grasped by an operator in order to avoid contact between the operator and the test portion 44 and or test composition 50.

In any embodiment, the test portion 44 can be a substantially smooth surface such as, for example, a portion of the stem 45, as illustrated in FIG. 1. Alternatively, the test portion may include additional (e.g., 3-dimensional) structural features. The additional structural features provide a greater challenge to a washing process because the structural features provide physical obstacles that hinder the removal of the test composition 50 from the test portion. In any embodiment, the test composition 50 can be applied as a liquid mixture and/or liquid suspension to the test portion 44 using processes that are known in the art including, for example, kiss coating, dip coating and spray coating. A portion or all of the liquid can subsequently be removed from the composition by evaporation (e.g., by placing the test element into a biosafety hood at ambient temperature (e.g., about 23° C.) for about 2-3 hours, for example). In the illustrated embodiment of FIG. 1, the test portion 44 is shown in partial section in order to show the test composition 50 coated on one side of the test portion and the underlying structure (e.g., stem 45) on the other side of the test portion. In any embodiment, the test composition 50 may be coated on the entire circumference of the test portion.

FIG. 2 shows one embodiment of a test element 41 having a test portion 44 with 3-dimensional structural features. The test element 41 can be used in any embodiment of the monitoring devices, methods, and systems of the present disclosure. The test portion 44 comprises a foam material 46 that is imbued with the test composition 50. The foam material 46 comprises individual cells or void spaces in which and to which the test composition 50 can be releasably adhered. Suitable foam materials for use in a test portion 44 of the present disclosure should releasably retain the test composition 50 thereon and, in particular, should releasably retain the tracer analyte. Non-limiting examples of suitable foam materials include polyurethane foams, polyethylene foams, and polystyrene foams. In some embodiments, the foams may be treated (e.g., corona-treated or electron beam-treated) in order to make the surface of the polymer more hydrophilic. The foam material 46 can be coupled to the stem 45, if present, or handle 49 using materials (e.g., melt bond, ultrasonic weld, adhesives, mechanical fasteners, or the like) and processes known in the art. In the illustrated embodiment of FIG. 2, the test portion 44 is shown in partial section in order to show the test composition 50 coated on one side of the test portion and the underlying structure (e.g., foam material 46) on the other side of the test portion. In any embodiment, the test composition 50 may be coated on the entire circumference of the test portion.

FIG. 3 shows an alternative embodiment of a test element 42 having a test portion 44 with 3-dimensional structural features. The test element 42 can be used in any embodiment of the monitoring devices, methods, and systems of the present disclosure. The test portion 44 comprises a fibrous material 47. The fibrous material 47 may comprise nonwoven fibers, as shown in FIG. 3, or woven fibers (not shown). The fibrous material comprises individual fibers with void spaces there between. The test composition can be releasably adhered to the surface of the fibers and, optionally, may fill void spaces between the fibers. Suitable fibrous materials for use in a test portion 44 of the present disclosure should releasably retain the test composition 50 thereon and, in particular, should releasably retain the tracer analyte. Non-limiting examples of suitable fibrous materials include cotton, DACRON polyester, rayon, nylon, flocked nylon, polyester, polypropylene, polyethylene. In some embodiments, the fibrous material may be treated (e.g., corona-treated, electron beam-treated, or coated with diamond-like glass) in order to make the surface of the material more hydrophilic. The fibrous material can be coupled to the stem 45, if present, or handle 49 using materials (e.g., adhesives, mechanical fasteners, or the like) and processes (e.g., fiber entanglement) known in the art. In the illustrated embodiment of FIG. 3, the test portion 44 is shown in partial section in order to show the test composition 50 coated on one side of the test portion and the underlying structure (e.g., fibrous material 47) on the other side of the test portion. In any embodiment, the test composition 50 may be coated on the entire circumference of the test portion.

FIG. 4 shows another alternative embodiment of a test element 43 having a test portion 44 with 3-dimensional structural features. The test element 43 can be used in any embodiment of the monitoring devices, methods, and systems of the present disclosure. The test portion 44 in this embodiment comprises one or more cavity 48. In this embodiment, the stem 45 and test portion 44 may be formed as a unitary part or may be formed as separate parts that are coupled together (e.g., by friction fit or via an adhesive). The test portion 44 may be formed at least in part of relatively rigid polymer (e.g., nylon, polysulfone, polycarbonate, or combinations thereof) or it may be formed using a more compliant polymer, such as silicone. Suitable materials for test portion 44 include, but are not limited to, any thermoplastic materials suitable for casting, profile extrusion, molding (e.g., injection molding) or embossing including, for example, polyolefins, polyesters, polyamides, poly(vinyl chloride), polymethyl methacrylate, polycarbonate, nylon, and the like. In other embodiments, test portion 44 may be formed by molding or embossing a sheet of suitable material into the desired cavity structure. In some embodiments, the test portion 44 may be treated (e.g., corona-treated or electron beam-treated) in order to make the surface of the material more hydrophilic. In the illustrated embodiment of FIG. 4, the test portion 44 is shown in partial section in order to show the test composition 50 coated on one side of the test portion and the underlying structure (e.g., cavities 48) on the other side of the test portion. In any embodiment, the test composition 50 may be coated on the entire circumference of the test portion.

In any embodiment, the test portion can comprise a porous fibrous nonwoven matrix (not shown). In any embodiment, the nonwoven matrix can comprise a wet-laid fiber matrix fabricated from polyethylene fibers (e.g., 1 denier fibrillated polyethylene fibers), nylon fibers (e.g., 6 denier, 5.08-cm chopped nylon fibers), bicomponent polymeric fibers (e.g., 1 denier bicomponent ethylene vinyl acetate/polypropylene fibers), or glass fibers. In any embodiment, the tracer analyte (e.g., a plurality of viable microorganisms as described herein) can be disposed on and/or in the fibrous nonwoven matrix. Processes for the production of suitable wet-laid fiber matrixes are described, for example in International Publication No. WO 2012/078426, which is incorporated herein by reference in its entirety.

In any embodiment, the test portion further comprises a plurality of inorganic particles such as the concentration agent particles (e.g., amorphous silicates of metals such as magnesium, calcium, zinc, aluminum, iron, titanium, and the like, and combinations thereof) described in International Patent Publication No. WO 2009/085357, which is incorporated herein by reference in its entirety. In any embodiment, the plurality of inorganic particles can be dispersed in the fibrous nonwoven matrix described herein. In any embodiment, when the tracer analyte comprises a plurality of viable microorganisms, the plurality of microorganisms can be adhered (e.g., releasably adhered) to two or more of the plurality of inorganic particles. International Patent Publication No. WO 2009/085357 discloses processes for binding a plurality of viable microorganisms to the inorganic particles of the present disclosure.

A person having ordinary skill in the art will recognize a variety of design configurations can be used for the one or more cavity in the test element 43. For example, International Publication No. WO 2009/134509, which is incorporated herein by reference in its entirety, discloses a variety of sample acquisition devices comprising cavities that are suitable for use as in a test portion 44 of a test element 43. International Patent Publication No. WO 1993/00994, which is incorporated herein by reference in its entirety, also discloses a sample acquisition device with a plurality of grooves capable of retaining a sample. One or more of the grooves described therein could be used in a test element according to the present disclosure.

In any embodiment, the test element may be configured to actuate (i.e., open) the frangible seal. Referring back to FIG. 4, the test element 43 comprises a piercing tip 52 that is shaped to puncture a frangible seal. Alternatively or additionally, the stem 45 of any test element can be formed from a material (e.g., wood, metal, plastic) that is rigid enough such that, when urged against a frangible seal, the stem can deform and/or rupture the frangible seal.

In any embodiment, the test portion of the test element can be shaped like a medical instrument or a part thereof. Advantageously, when the monitoring device of this embodiment is used to assess the efficacy of a washing process, the washing process is challenged to remove material (i.e., the test composition) from an object that may be similar to the actual medical instruments that are cleaned in the automated washer. In some embodiments, the test portion may comprise a hinge structure (e.g., a hinge structure found on a scissors or a medical clamp). Advantageously, in these embodiments, the removal of the test composition from the test portion more closely resembles actual conditions in a cleaning process.

The test composition is releasably adhered to the test portion of the test element. The test composition is dispersible, and may be soluble, in an aqueous solvent (e.g. an aqueous solvent used to was articles). The test composition comprises a tracer analyte. The tracer analyte is dispersible, and may be soluble, in an aqueous solvent (e.g. an aqueous solvent used to wash articles). A "tracer analyte", as used herein comprises a compound that can be quantitatively detected using a photo-optical device. The detection may be achieved by direct detection (e.g., using an optical property of the tracer analyte per se such as, for example the U.V-visible absorbance of the tracer analyte) or by indirect detection (e.g., using an optical property of a derivative or byproduct of the tracer analyte). In any embodiment, the tracer analyte can be a chemical compound that is capable of participating in a chemical reaction that, either directly or indirectly, results in a detectable product. "Chemical reaction", as used herein, includes binding reactions (e.g., ionic binding, covalent binding, or hydrophobic interaction), synthetic reactions, decomposition reactions, oxidation reactions, reduction reactions, complexation reactions, acid-base reactions, and photochemical reactions.

By way of example, in one embodiment, the tracer analyte comprises an unlabeled protein (e.g., bovine serum albumin) In this embodiment, the tracer analyte can be detected indirectly by reacting the tracer analyte with a protein-detecting detection reagent such as bicinchoninic acid, for example, thereby forming a byproduct (i.e., a purple-colored bicinchoninic acid-$Cu^{1+}$ chelate), which can be quantitated using a spectrophotometer device. By way of example, in another embodiment, the tracer analyte can comprise a labeled protein that undergoes a chemical reaction (e.g., a binding reaction, a hydrolytic reaction) to bind, release, or detectably modify the label and/or the labeled protein. By way of example, in yet another embodiment, the tracer analyte comprises adenosine-5'-triphosphate (ATP) or a molecule (e.g., ADP) that can be converted to ATP. In this embodiment, the ATP can be quantitatively detected, for example, by reacting it with luciferin and luciferase to cause the emission of a byproduct (light), which can be detected quantitatively using a luminometer. A person having ordinary skill in the art will recognize other compounds that are suitable for use as a tracer analyte and the particular detection reagent(s) and/or instrument(s) that can be used to detect and quantitate the tracer analyte.

In any embodiment, the tracer analyte can be selected from the group consisting of a plurality of viable microorganisms or a biomolecule associated therewith, an acid, a base, a nucleotide, a protein, a nucleic acid, a carbohydrate, or hemoglobin. The acid may comprise an organic acid (e.g., a fatty acid). The base may comprise an organic base (e.g., a basic amino acid such as arginine or lysine). The acid or base tracer analyte may be detected by U.V-visible absorbance or a pH-detecting detection reagent (e.g., a pH indicator) and quantitating the acid or base using a spectrophotometer, for example.

As discussed above, in any embodiment, the tracer element can comprise a plurality of viable microorganisms. Preferably, the viable microorganisms are generally regarded as non-pathogenic microorganisms. Suitable non-pathogenic microorganisms include, for example bacteria (e.g., probiotic bacteria such as *Lactobacillus* and *Bifidobacterium* species) and yeast (e.g., *Saccharomyces cerevisiae*), which can be detected by culture methods or by detecting biomolecules (e.g., proteins, nucleic acids, small molecules (e.g., ATP), and/or antigens) associated therewith. Suitable nonpathogenic microorganisms also include bacterial endospores (e.g., spores of *Bacillus atrophaeus* or *Geobacillus stearothermophilus*). Coatings comprising about $10^6$ to about $10^8$ spores can be detected by enzymes (e.g., glucosidases or proteases) associated therewith (see, for example, U.S. Pat. No. 5,073,488 and U.S. Patent Application Publication No. 2011/0182770; which are incorporated herein by reference in their entirety) or by using nucleic acid-binding dyes (see, for example, U.S. Patent Application Publication No. 2011/0200992, which is incorporated herein by reference in its entirety).

In any embodiment, the test composition further may comprise biological materials that are found in animal tissue, fluids, and/or excreta. Nonlimiting examples of said biological materials include blood cells, serum, bilirubin, mucin, and carbohydrates.

In any embodiment, the test composition further may comprise a dye that is visually detectable prior to exposing the test element to a washing process. Accordingly, the dye can permit visual confirmation that the test element has the test composition coated thereon.

In any embodiment, the test composition optionally may comprise a polymeric binder. Advantageously, the polymeric binder inhibits the dispersion of the tracer analyte in an aqueous solvent. Without being bound by theory, this inhibition occurs because the polymeric binder acts as a diffusion barrier to inhibit the release of the tracer element from the test portion. The polymeric binder rehydrates and dissolves into an aqueous washing solvent relatively slowly compared to the tracer analyte. In any embodiment, the polymeric binder may comprise polyvinyl alcohol (PVA). The polyvinyl alcohol can be prepared as an aqueous solution comprising the tracer analyte (e.g., 1 microgram/mL ATP), which is coated onto the test element and dried, as described herein. In any embodiment, the PVA-containing aqueous solution may comprise about 9 weight percent to about 11 weight percent PVA. In any embodiment, the polymeric binder may comprise polyethylene glycol (PEG 8000, which has a molecular weight of approximately 8,000 daltons). The polyethylene glycol can be prepared as an aqueous solution comprising the tracer analyte (e.g., 1 microgram/mL ATP), which is coated onto the test element and dried, as described herein. In any embodiment, the PEG-containing aqueous solution may comprise about 50 weight percent PEG.

In any embodiment, the test composition may be prepared as a homogeneous mixture in a suitable solvent (e.g., water and/or an alcohol). In any embodiment, the test composition may be dissolved or suspended in an organic solvent before it is applied to the test element. Advantageously, this may permit the application of higher concentrated solutions of tracer analyte (or other components of the test composition) wherein the tracer analyte and/or component is dissolved at a concentration that exceeds the water solubility of the tracer analyte or component.

In any embodiment, the test composition can be applied as a single solution and/or suspension to the test portion of the test element (e.g., using processes described herein) in a single application. Alternatively, the test composition can be applied to the test portion of the test element as two or more separate solutions and/or suspensions. For example, a first solution and/or suspension comprising the tracer analyte may be applied to the test element and a second solution and/or suspension comprising a polymeric binder may be applied separately to the test element. Optionally, the first solution and/or suspension may be permitted to dry or partially dry before the second solution and/or suspension is applied.

In any embodiment, the monitoring device can comprise a test element that is adapted to deliver a liquid to the container. Nason (U.S. Pat. No. 5,266,266; which is incorporated herein by reference in its entirety) discloses a specimen test unit that includes a swab member that can be adapted to function as a test element according to the present disclosure. FIGS. 5A-C show a portion (i.e., the portion proximate the first end 112 of the container 110) of one embodiment of a test element 140 that is adapted to deliver a second solvent 175 to the container 110. In this embodiment, the handle 149 comprises a hollow channel 162 extending there through. Coupled to the handle 149 (e.g., via an adhesive (not shown) or by friction fit) is a reservoir 164 with a hollow stem 145 coupled thereto (e.g. by friction-fit).

A portion 180 of the hollow stem 145 disposed in the reservoir 164 comprises a liquid flow regulator (e.g., a breakable liquid flow regulator) capable of placing the reservoir in fluid communication with the hollow stem 145. The portion 180 includes a solid rod segment 182 and a score 184 that facilitates the breakage of the stem 145, thereby creating a stem opening 186 to permit liquid flow through out of the reservoir through the hollow stem 145. The test element 140 can be made as described by Nason. As shown in FIG. 5B, (e.g., manual pressure) pressure against the flexible reservoir 164 in the direction of arrow "A" causes the reservoir 164 to deflect against the rod segment 182, causing the score 184 to fracture and optionally separate from the hollow stem 145 (as shown in FIG. 5C), which permits the flow of second solvent 175 through the stem opening 186 and into the hollow stem 145, as shown by arrow "B". A person having ordinary skill in the art will recognize other liquid flow regulator means (e.g., frangible ampoules and other means disclosed in U.S. Pat. Nos. 4,978,504 and 5,879,635, which are incorporated herein by reference in their entirety) that can be used to place the second solvent 175 in the reservoir 164 into fluid communication with the hollow stem 145.

In any embodiment, the second solvent 175 can be a liquid in which a portion (e.g., the tracer analyte) or all of the test composition (not shown) is soluble. In any embodiment, the second solvent 175 may comprise water. In some embodiments, the second solvent 175 additionally comprises a buffer component to maintain the solvent within a predefined pH range (e.g., a pH range that is suitable for a reaction used in the detection of the tracer analyte). In some embodiments, the solvent may comprise a surfactant (e.g., a nonionic surfactant) to facilitate the dispersion of the tracer analyte and/or test composition 50 into the second solvent 175. A suitable surfactant does not substantially interfere with a reaction, a detection reagent, and/or instrument that is used for the detection of the tracer analyte. In any embodiment the second solvent 175 may be the same as the first solvent (not shown), if present in the monitoring device.

Figure 6:
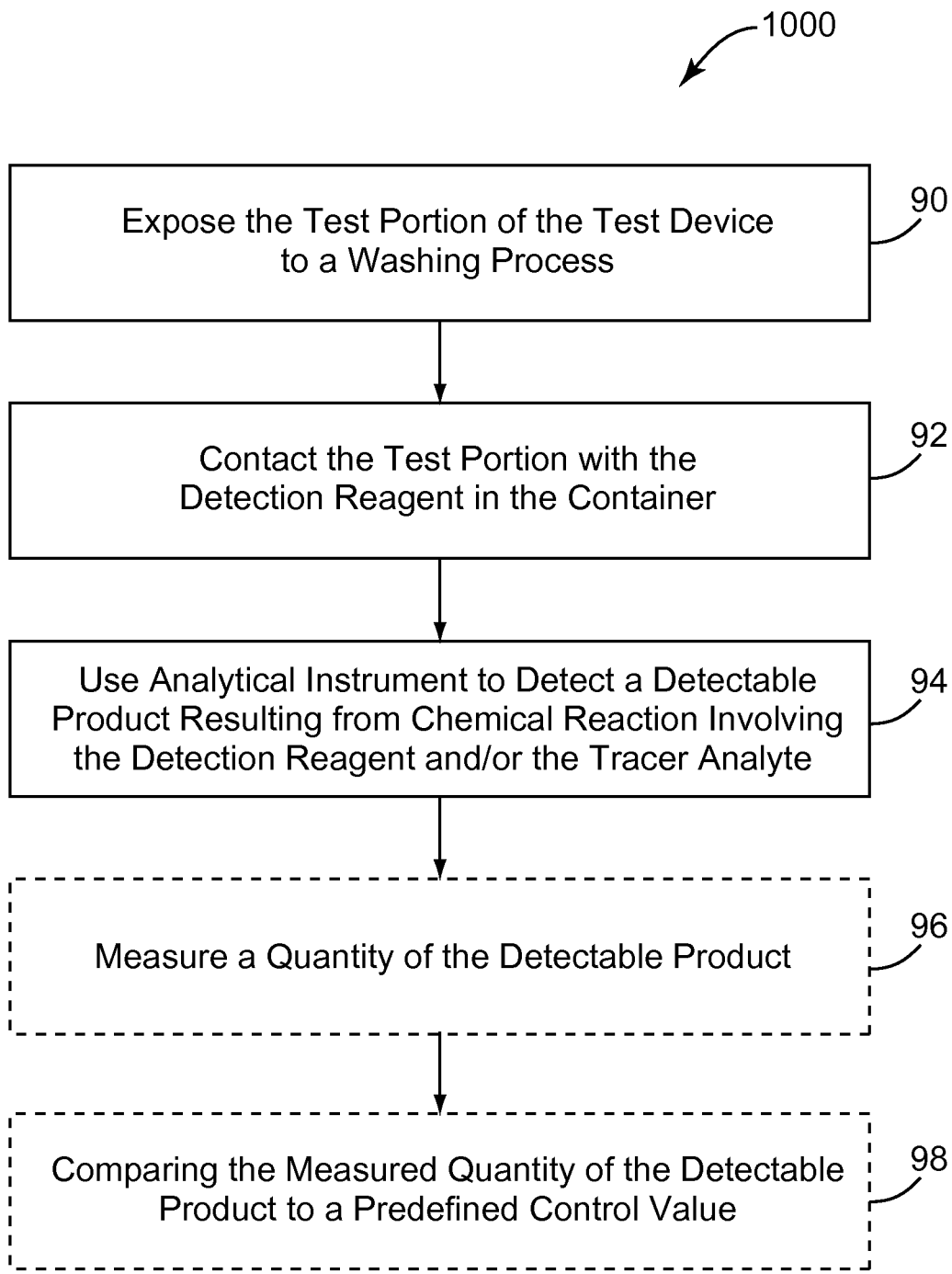
FIG. 6 is a block diagram of one embodiment of a method of assessing the efficacy of a washing process according to the present disclosure.

In another aspect, the present disclosure provides a first method. For example, the present disclosure provides a first method of assessing the efficacy of a washing process. FIG. 6 shows a block diagram of one embodiment of a first method of assessing the efficacy of a washing process according to the present disclosure. The first method 1000 comprises the step 90 of exposing to the washing process the test portion of any embodiment of a monitoring device according to the present disclosure, the step 92 of contacting the test portion of the test element with the detection reagent in the container of the monitoring device, and the step 94 of using an analytical instrument to detect a presence or an absence of the detectable product resulting from the one or more chemical reaction in which the detection reagent and the tracer analyte are capable of participating.

Exposing the test portion of the test element to the washing process can comprise placing the test element into an automated washer. In any embodiment, the automated washer can comprise an automated washer disinfect such as a GETINGE 46-series washer disinfector (available from Getinge USA, Inc., Rochester, N.Y.), for example. During normal handling and use, the test element typically is grasped and/or secured preferably using its handle, if present, or its stem. In any embodiment, the test element can be placed in a rack, which is placed in the automated washer prior to exposing the test element to the washing process.

Optionally, the test element can be secured to the rack or to a structure (e.g., a rack or shelf) in the automated washer.

Figure 10:
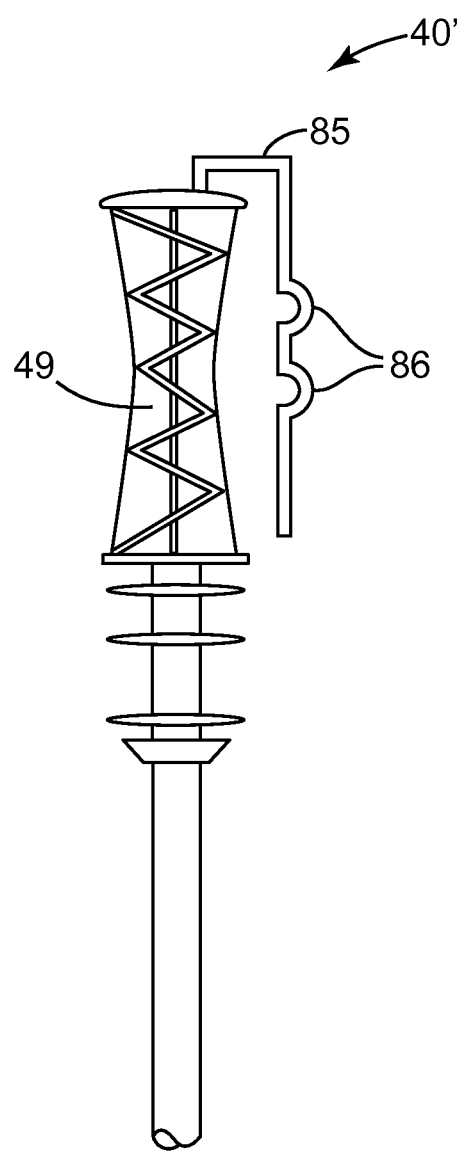
FIG. 10 is a side view of the handle portion of one embodiment of a monitoring device comprising a secural element according to the present disclosure.

In any embodiment, the test element further may comprise a secural structure configured to detachably secure the test element to a structure (e.g., a rack or shelf) in the automated washer. FIG. 10 shows a portion (i.e., the portion proximate the handle) of one embodiment of test element 40' comprising a secural element 85. In some embodiments, the secural element 85 may be formed (e.g., by a molding process) of the same material as the handle 49. The secural element 85 can be shaped and dimensioned to include one or more engagement structures 86 that can releasably hold a portion of an automated washer rack or wire basket, for example, and thereby hold the monitoring device at a fixed location within an automated washer. In some embodiments, the secural element 85 can be formed separately and attached to the test element 40' using an attachment means known in the art (e.g., an adhesive, a thermal bond, an ultrasonic weld, a screw, a rivet, or the like). The secural element can be fabricated from any material that is not substantially degraded by a washing process. Non-limiting examples of suitable materials include metal and polymeric (e.g., polypropylene, polyethylene) materials.

Securing the test element may be performed using a zip-tie, a clamp (e.g., a hose clamp), or the like. In any embodiment, the test portion may be placed in the automated washer at a peripheral location within the washing chamber, thereby testing the efficacy of the washing process in a difficult-to-reach location.

Many commercial automated washers are programmable and are configured with preset washing cycles. Accordingly, exposing the test portion of the test element to the washing process can comprise placing the test portion into an automated washer and performing at least a portion of an automated wash cycle while the test portion is disposed in the automated washer. An automated washing cycle may comprise, for example, one or more pre-rinse step, one or more wash step, one or more rinse step, one or more drying step, or a combination of any two or more of the foregoing steps. After exposing the test portion to at least a portion of the automated washing cycle, the amount of tracer analyte remaining on the test element can be analyzed to determine whether the washing cycle removed any or all of the tracer analyte from the test element, thereby indicating the washing efficacy of the portion of the automated washing cycle.

In a preferred embodiment, exposing the test portion of the test element to the washing process comprises placing the test portion into an automated washer and performing a complete automated wash cycle while the test portion is disposed in the automated washer. A non-limiting example of a preset automated washing cycle includes the following steps: a 1-minute pre-rinse step using cold water, a 5-minute washing step using hot (e.g., 60° C.) water mixed with an enzyme detergent (e.g., a multi-enzyme detergent), two 1-minute rinse steps with hot water, a 1-minute disinfection step with very-hot (e.g., 90° C.) deionized water, and a 10-minute drying step. Thus, after exposing the test portion to the complete automated washing cycle, the amount of tracer analyte remaining on the test element can be analyzed to determine whether the washing cycle removed any or all of the tracer analyte from the test element.

Figure 7:
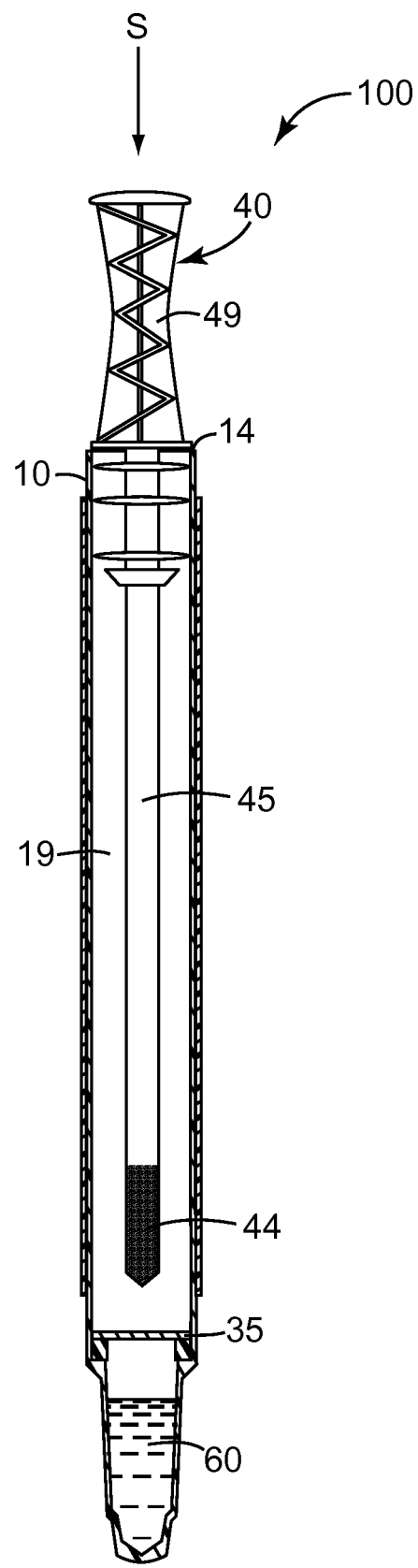
FIG. 7 is a side view, partially in section of the assembled monitoring device of FIG. 1 with the test element disposed in a first operational position with respect to the container.

Typically, while the test portion is exposed to the washing process, the container is kept in a location outside the automated washer. After the test portion has been exposed to the washing process, the test element can be removed (e.g., from the automated washer) and inserted into the receiving chamber of the container. FIG. 7 shows a side view, partially in section of one embodiment of a monitoring device 100 with the test element inserted into the container. In the illustrated embodiment, the test element 40 is disposed in a first operational position with respect to the container 10. In the first operational position, a first portion of the test element (e.g., the test portion 44 and stem 45) are disposed in the receiving chamber 19 of the container 10 and a second portion of the test element (e.g., the handle 49) is operationally coupled (e.g., by friction fit) with the container 10 proximate the opening 14 of the container.

Figure 8:
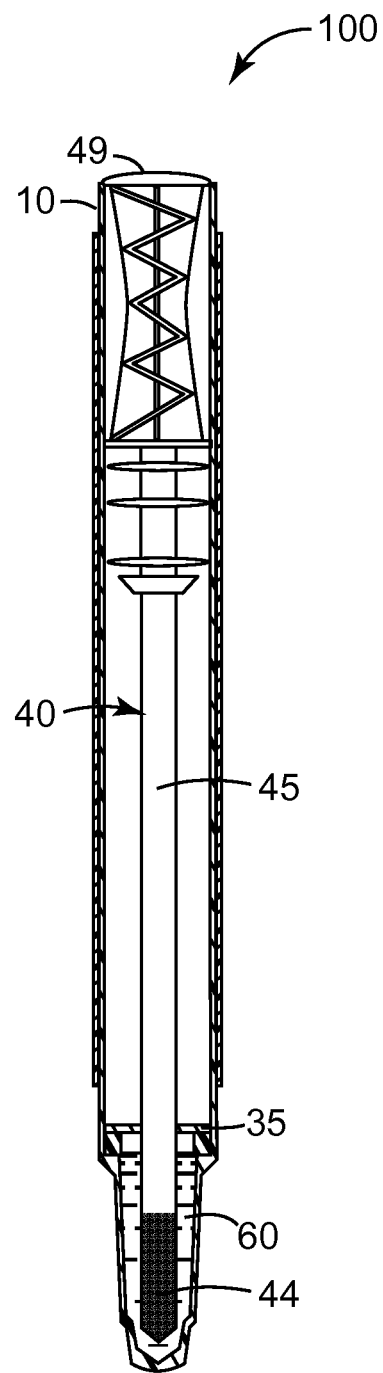
FIG. 8 is a side view, partially in section of the assembled monitoring device of FIG. 1 with the test element disposed in a second operational position with respect to the container.

The first method of the present disclosure comprises contacting the test portion of the test element with the detection reagent in the container of the monitoring device. In the illustrated embodiment of FIGS. 7-8, this comprises moving (e.g., by applying manual pressure to the handle in the direction of arrow "S") the test element 40 into a second operational position with respect to the container 10, as shown in FIG. 8. In the second operational position, the test element 40 has pierced the frangible seal 35 and the test portion 44 is contacting the first solvent 60, in which the detection reagent (not shown) is dissolved. By way of example, the tracer analyte can be ATP and the first solvent 60 may be an aqueous solution with a pH that is suitable to facilitate the reaction of a detection reagent (e.g., luciferase enzyme) with luciferin and the tracer analyte (ATP).

In any embodiment, contacting the test portion of the test element with the solvent in the container of the monitoring device can further comprise dissolving the tracer analyte and/or test composition into the solvent.

Referring back to FIG. 6, the first method 1000 of the present disclosure comprises the step 94 of using an analytical instrument to detect a presence or an absence of the detectable product resulting from the one or more chemical reaction in which the detection reagent and the tracer analyte are capable of participating. In any embodiment, the detectable product can be a colored compound (e.g., a bicinchoninic acid-Cu+ chelate formed by the reaction of protein with $Cu^{2+}$ in the presence of bicinchoninic acid) having a detectable absorbance spectrum. In these embodiments, the detectable product can be detected using a spectrophotometer, for example. In any embodiment, using an analytical instrument to detect a presence or an absence of the detectable product can comprise inserting at least a portion (e.g., a cuvette portion) of the container of the monitoring device into the analytical instrument. In any embodiment, the detectable product can be electromagnetic radiation (e.g., visible light, such as the light emitted by the reaction of luciferin and luciferase with ATP, for example) having a certain wavelength (e.g., about 550 nm to about 620 nm).

Optionally, the first method 1000 of the present disclosure further can comprise the step 96 of using the analytical instrument to measure a quantity of the detectable product. In preferred embodiments, the quantity of detectable product is proportional to the quantity of tracer analyte, if present, on the test element. In any embodiment, the measured quantity can be a threshold detectable quantity, which simply indicates the presence or absence of the detectable product. A person having ordinary skill in the relevant art will recognize the threshold detectable quantity represents the lower limit of detection and is defined by several parameters including, for example, the reactants, the container, and the analytical instrument. In any embodiment, the measured quantity can be an absolute quantity, which can be determined by comparing the detectable quantity to a standard or a plurality of standards, for example. In any embodiment, the measured quantity can be a relative quantity (e.g., relative light units detected from a light-emitting reaction).

Optionally, the first method 1000 of the present disclosure further can comprise the step 98 of comparing the measured quantity of the detectable product to a predefined standard (i.e., a "control value"). The control value can be selected to indicate a quantity (e.g., a maximum quantity) of detectable product associated with an adequate washing cycle. Thus, in these embodiments; when the washing cycle is adequate to remove a sufficient quantity of soil (e.g., the tracer analyte) from the test element, the quantity of detectable product may be less than or equal to the control value.

In another embodiment of the first method, the standard may be a measurable quantity of tracer analyte that is detected from a test element (e.g., a "control" test element) that has not been exposed to a washing cycle. In this embodiment, an indication of exposure to an adequate washing cycle can be that the washed test element retains a predetermined percentage (e.g., up to about 50%, up to about 40%, up to about 30%, up to about 25%, up to about 20%, up to about 15%, up to about 10%, up to about 5%, up to about 2%, up to about 1%) of the tracer analyte that is detectable from the control test element.

In any embodiment, the first method further comprises using at least one measured quantity of tracer analyte to define an action limit. Action limits for controlling a multi-step decontamination process are disclosed in International Patent Publication No. WO 2012/112482, which is incorporated herein by reference in its entirety. In any embodiment, the first method further can comprise comparing a measured quantity of tracer analyte to a predefined action limit.

In another embodiment of the first method, the standard may be an arbitrary value (e.g., relative light units, micrograms of tracer analyte, or the like) that is selected (e.g., by the user or the provider of the test element) to indicate the efficacy of the washing process.

In any embodiment, an operator may desire to keep a record of the detection of a presence or measureable quantity of tracer analyte detected from a test element exposed to a particular washing process. In some embodiments, the record may be an electronic record that is stored on a computer-readable medium using electronic data storage processes that are well-known in the art. The computer-readable medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like.

In any embodiment of the first method, an operator may desire to associate a first datum (e.g., the record of the detection of a presence or measureable quantity of tracer analyte detected from a test element) with a second datum (e.g., other information related to the test element). In any embodiment, the second datum comprises information selected from the group consisting of a date, a time, a washing apparatus, an operator, an instrument to be washed, and a combination of two or more of any of the foregoing test data. Advantageously, associating the first datum with the second datum can allow the operator to verify that a particular instrument was present in an automated washer with a test element that verified the efficacy of the washing process to which both the instrument and the test element were exposed.

In any embodiment of the first method, exposing the test portion of a test element to a washing process can comprise exposing the test portions of a plurality of test elements to a washing process. Advantageously, this embodiment can be used to identify certain spatial regions within an automated washer that do not wash objects as effectively as other spatial regions within the automated washer. This type of information can be used by the operator to make decisions such as preventative maintenance schedules and/or load configurations, for example, for particular automated washers. In these embodiments, a first monitoring device can be positioned at a first predefined location (e.g., upper rack proximate the back of the washer) and a second monitoring device can be positioned at a second predefined location (lower rack proximate the front of the washer). After exposing the first and second monitoring devices to a washing process, the tracer analyte remaining on the test portion of each monitoring device is measured as described herein and each measured quantity can be compared to a control value and/or can be compared to each other. The control value may indicate the monitoring devices were exposed to an effective washing process or it may indicate the monitoring devices were exposed to an ineffective washing process. According to this embodiment, the first method can be used to create a 2-dimensional or 3-dimensional map of the interior of an automated washer, the map showing specific regions of the washer and the washing efficacy of each region.

In any embodiment, the first method optionally can comprise the step of placing the test portion of the monitoring device in a receiver configured to restrict fluidic accessibility to the test portion. In some embodiments, the receiver may comprise a wall that shields the test portion from a direct spray of wash solvent (e.g., water) emitted from a nozzle or orifice in the automated washer. Thus, in order for the wash solvent to impinge on the test portion, it must take an indirect path (e.g., by deflection off a wall or other object present in the automated washer. In some embodiments, placing the test portion of the monitoring device in a receiver configured to restrict fluidic accessibility to the test portion comprises placing the test portion into an interior space of a lumened object. Exemplary lumened objects include, for example, tubes, scopes, and the like.

In yet another aspect, the present disclosure provides a second method of controlling a decontamination process. The second method comprises processing as a single batch in a decontamination process an object having an unknown amount of biological soil disposed thereon and/or therein and a monitoring device comprising a predetermined quantity of tracer analyte according to any one of the embodiments of the monitoring device of the present disclosure. The second method further comprises, after exposing the test portion to the decontamination process, contacting the test portion with the detection reagent in the container; and using the analytical instrument to detect a presence or an absence of the detectable product, wherein the presence of the detectable product indicates a presence of the tracer analyte on the test portion after exposing the test portion to the washing process. The decontamination process may be a multi-step decontamination process including, without limitation, subprocesses such as soaking, wiping, brushing, scrubbing, washing, contact with a disinfecting agent, contact with a sterilizing agent, a combination of any two or more of the foregoing subprocesses or it may be an single process such as any of the aforementioned subprocesses.

"Processing as a single batch" for the purposes of the present disclosure and claims means the object (e.g., a medical instrument that was used in a medical or surgical procedure) is placed with the monitoring device of the present disclosure into a single container (e.g., a tub, wash basin, automated washer, or the like) for the purpose of exposing the object and the monitoring device to substantially similar decontamination conditions (e.g., solvent, detergent, temperature, flow rates, and/or rinse volume). In any embodiment of the second method, processing as a single batch in a decontamination process the object and the monitoring device comprises processing as a single batch in a decontamination process the object and a plurality of the monitoring devices. In any embodiment of the second method, processing a plurality of monitoring devices can comprise processing a first monitoring device at a first location (e.g., a first location in an automated washer or automated washer-disinfector) and processing a second monitoring device at a second location that is spaced apart from the first location (e.g., a second location in the automated washer or the automated washer-disinfector).

Contacting the test portion with the detection reagent in the container comprises contacting the test portion with the detection reagent in the container of the monitoring device of the present disclosure in order to produce a detectable product, as described herein. A presence of the detectable product indicates at least a portion of the tracer analyte was not released from the test element while the test portion was exposed to the decontamination process, as described herein. In any embodiment of the second method, processing the object and the monitoring device in a decontamination process comprises processing the object and the monitoring device in an automated washer or an automated washer-disinfector.

In any embodiment of the second method, detecting a presence or an absence of the detectable product further comprises calculating a quantity of tracer analyte remaining on the test portion after exposing the test portion to the decontamination process. In any embodiment, the second method further comprises comparing the quantity of tracer analyte remaining on the test portion of at least one monitoring device after exposing the test portion to the decontamination process to a predetermined quantity of tracer analyte associated with an action limit. "Action limit", as used herein refers to a threshold amount of biological analyte, detected in the residue collected from an article according to a pre-defined sample collection method and a pre-defined analyte detection method, which indicates a particular sub-process or a series of sub-processes failed to remove or inactivate an acceptable amount of biological soil from the article. Action limits can be used to determine what activities (e.g., re-processing the load, equipment maintenance), if any, should be taken as a result of inadequate removal of the tracer analyte from the monitoring device.

In any embodiment of the second method, if the quantity of tracer analyte remaining on the test portion of the at least one monitoring device after exposing the test portion to the decontamination process is less than or equal to the predetermined quantity (e.g., an "action limit"), the method further comprises releasing the object for use (e.g., for use in a subsequent procedure or for use in a first subsequent process (e.g. a wrapping step and/or a sterilization step to prepare the object for re-use in a medical or surgical procedure). Conversely, in any embodiment of the second method, if the quantity of tracer analyte remaining on the test portion of the at least one monitoring device after exposing the test portion to the decontamination process is greater than or equal to the predetermined quantity, the method further comprises releasing the object for use in a second subsequent process (e.g., re-washing, re-processing, additional cleaning treatments, or the like).

In yet another aspect, the present disclosure provides a kit. The kit comprises a container as disclosed herein, the container comprising a first end with an opening and a second end opposite the first end, wherein the container includes a detection reagent disposed therein. The kit further comprises a test element comprising a test portion to which a test composition is releasably adhered, wherein the test composition comprises a predetermined quantity of tracer analyte. The test element comprises any suitable tracer analyte according to the present disclosure. The detection reagent comprises any detection reagent suitable to participate in a chemical reaction to detect, directly or indirectly, the tracer analyte. The container is configured to receive the test portion and configured to be operationally coupled to an analytical instrument, as described above. The tracer analyte and the detection reagent each are capable of participating in one or more chemical reaction that results in the formation of a detectable product, wherein the detectable product indicates a presence and, optionally, a quantity of tracer analyte in the one or more chemical reaction.

In any embodiment of the kit, the tracer analyte is selected from the group consisting of a plurality of viable microorganisms or a biomolecule associated therewith, an acid, a base, a nucleotide, a protein, a nucleic acid, a carbohydrate, or hemoglobin. In any embodiment, the test portion comprises a fibrous nonwoven matrix, as described hereinabove. In any embodiment wherein the analyte comprises a plurality of viable microorganisms, the plurality of viable microorganisms may be disposed on or in the fibrous nonwoven matrix. In any embodiment of the kit, the test portion further comprises a plurality of inorganic particles dispersed in the fibrous nonwoven matrix. In these embodiments, the plurality of viable microorganisms can be releasably adhered to two or more of the plurality of inorganic particles.

In any embodiment of the kit, a portion of the test element can be disposed in the container (e.g., in a first operational position, as described herein. In any embodiment, the container further comprises a first solvent disposed therein (e.g., in the cuvette chamber, as disclosed herein). In any embodiment of the kit, the test element further comprises a reservoir with a solvent disposed therein, wherein the test element comprises a hollow stem, as described herein, and the reservoir comprises a liquid flow regulator (e.g., a breakable liquid flow regulator) capable of placing the reservoir in fluid communication with the hollow stem, as described herein.

In any embodiment, the kit further may comprise a means to secure a test element. The means to secure the test element may comprise a clamp, a string, a wire, a zip-tie, or any other suitable means capable of securing the test element to an object (e.g., a medical instrument, a shelf, a wire basket) in an automated washer.

In any embodiment, the kit further may comprise a process challenge device. A "process challenge device", as used herein, refers to a water-insoluble container (e.g., an envelope, a tube, an elongated tube, a box) with at least one opening and an inner volume defined by at least one wall. In any embodiment, the process challenge device may comprise one or more walls with a plurality of openings. The process challenge device is configured to receive at least part of the test portion of any embodiment of the test element of the present disclosure. In any embodiment, the process challenge device may be configured to receive the entire test portion of any embodiment of the test element of the present disclosure. In any embodiment, the process challenge device may be configured to receive the entire test element of any embodiment of the present disclosure.

Figure 11:
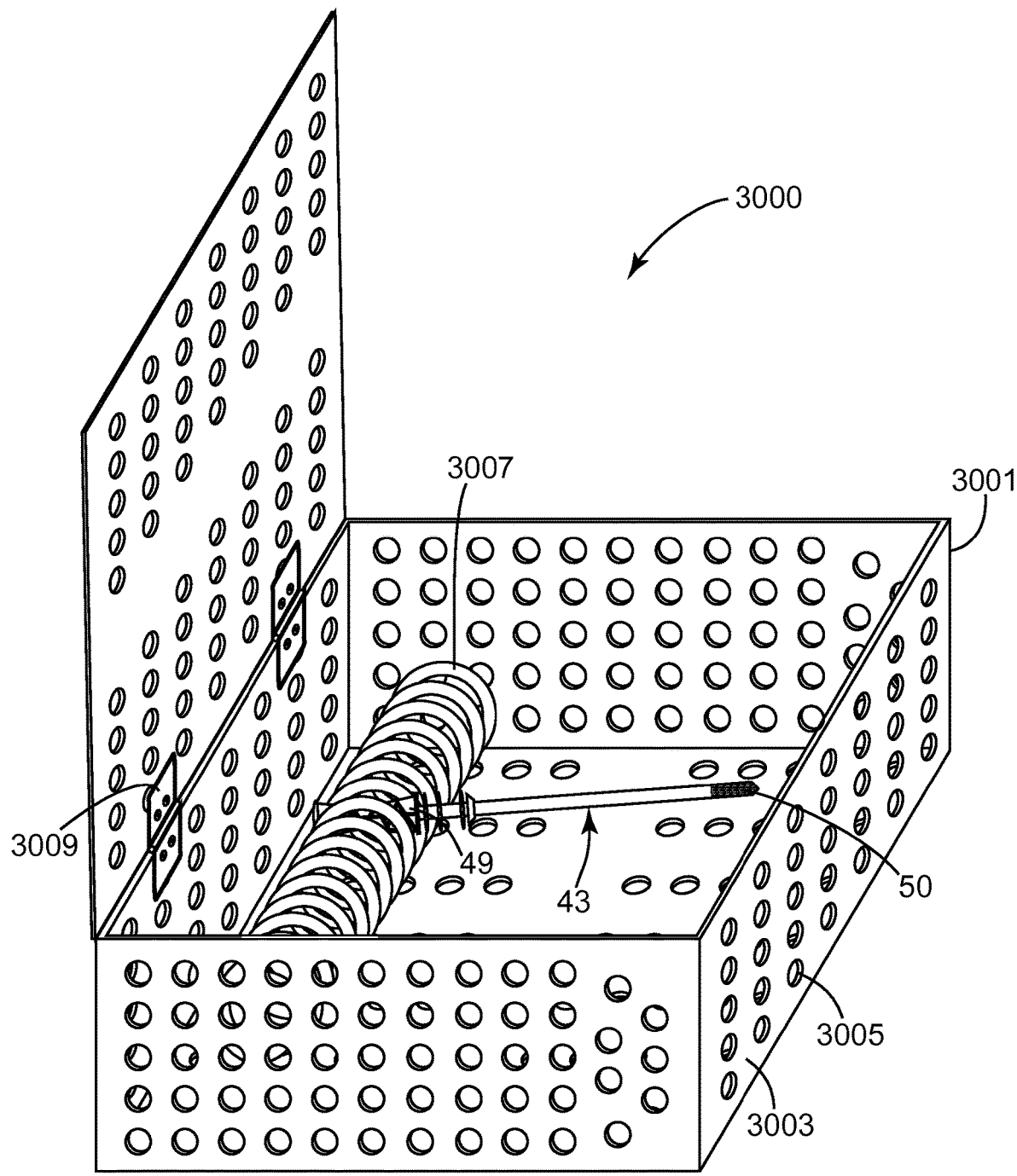
FIG. 11 is a perspective view of one embodiment of a process challenge device, in an open configuration with a test element disposed therein, according to the present disclosure

FIG. 11 shows one embodiment of a process challenge device 3000 according to the present disclosure. The process challenge device 3000 comprises a water-insoluble container 3001 having at least one wall 3003. The process challenge device 3000 comprises a plurality of walls 3003 that can be configured to surround an object placed in the process challenge device 3000. Optionally, one of the walls is hingedly attached to another wall via a hinge means 3009, thereby permitting the process challenge device 3000 to be placed into an open configuration (as illustrated in FIG. 11) or in a closed configuration (not shown). In the open configuration, the process challenge device 3000 can receive a test element such as test element 43, for example. The test element can be any embodiment of a test element according to the present disclosure. In a preferred embodiment, the test element 43 is a test element from a monitoring device (not shown) of the present disclosure.

The at least one wall 3003 presents a physical impediment (i.e., challenge) to hinder the passage of process fluid (e.g., water and/or detergent) from a washer or washer-disinfector to an object (e.g., a test element) disposed in the process challenge device 3000. In any embodiment, the severity of the challenge can be attenuated by providing relatively greater access (i.e., pathways) to the test element. Thus, optionally, at least one wall 3003 of the one or more walls of the process challenge device 3000 comprises at least one hole 3005 extending therethrough. The at least one hole 3005 can be any size (e.g., diameter) that is suitable to permit the passage of a fluid therethrough. In a particular embodiment, the size of the holes 3005 are similar, as illustrated in FIG. 11. In another particular embodiment (not shown), the size of the holes 3005 are different. The holes 3005 may be about 1 mm to about 10 mm or greater in diameter, for example.

In any embodiment, at least one wall 3003 of the one or more walls of the process challenge device 3000 comprises a plurality of holes 3005 extending therethrough. In any embodiment, a plurality of walls 3003 of the one or more walls of the process challenge device 3000 comprises a plurality of holes 3005 extending therethrough, as shown in FIG. 11. The holes 3005 permit the passage of process fluid (not shown) therethrough.

In any embodiment, the process challenge device 3000 optionally comprises means 3007 for securing an object (e.g., test element 43) in the process challenge device 3000. In the illustrated embodiment of FIG. 11, the means 3007 comprises a spring-like structure capable of entrapping a portion (e.g. handle 49 of test element 43) of the object. A person having ordinary skill in the art will recognize other suitable means such as, for example, a clip, a clamp, a hook, a tether, an adhesive, a weighted object, and the like. In any embodiment, the means 3007 secures the test element 43 such that the test composition 50 is held in a generally predetermined position within the process challenge device 3000.

In use, the process challenge device 3000, with the test element 43 disposed therein, can be placed in any suitable location in a washer or washer-disinfector. The washer or washer-disinfector can be operated according to various operating parameters (e.g., standard operating parameters) and the test element 43 can be removed subsequently and tested as described herein in order to determine whether the test composition 50 was adequately dislodged from the test element during the operating cycle. Accordingly, in any embodiment of the methods of assessing the efficacy of a washing process, the method further comprises, before exposing the test portion of the monitoring device to the washing process, positioning at least a part of the test portion of the monitoring device in a process challenge device.

Process challenge devices of the present disclosure can be made from suitable water-insoluble materials (e.g., stainless steel, aluminum, polymers such as HDPE or polycarbonate, for example) according to conventional processes (e.g., molding) known in the art. In any embodiment, the material(s) from which the process challenge device is made can be relatively rigid, relatively flexible, or may contain a portion that is relatively rigid and a portion that is relatively flexible. In any embodiment, the hinge means 3009, if present, may comprise a spring hinge or biasing hinge that is adapted to hold the device 3000 in a normally-closed configuration.

Figure 9:
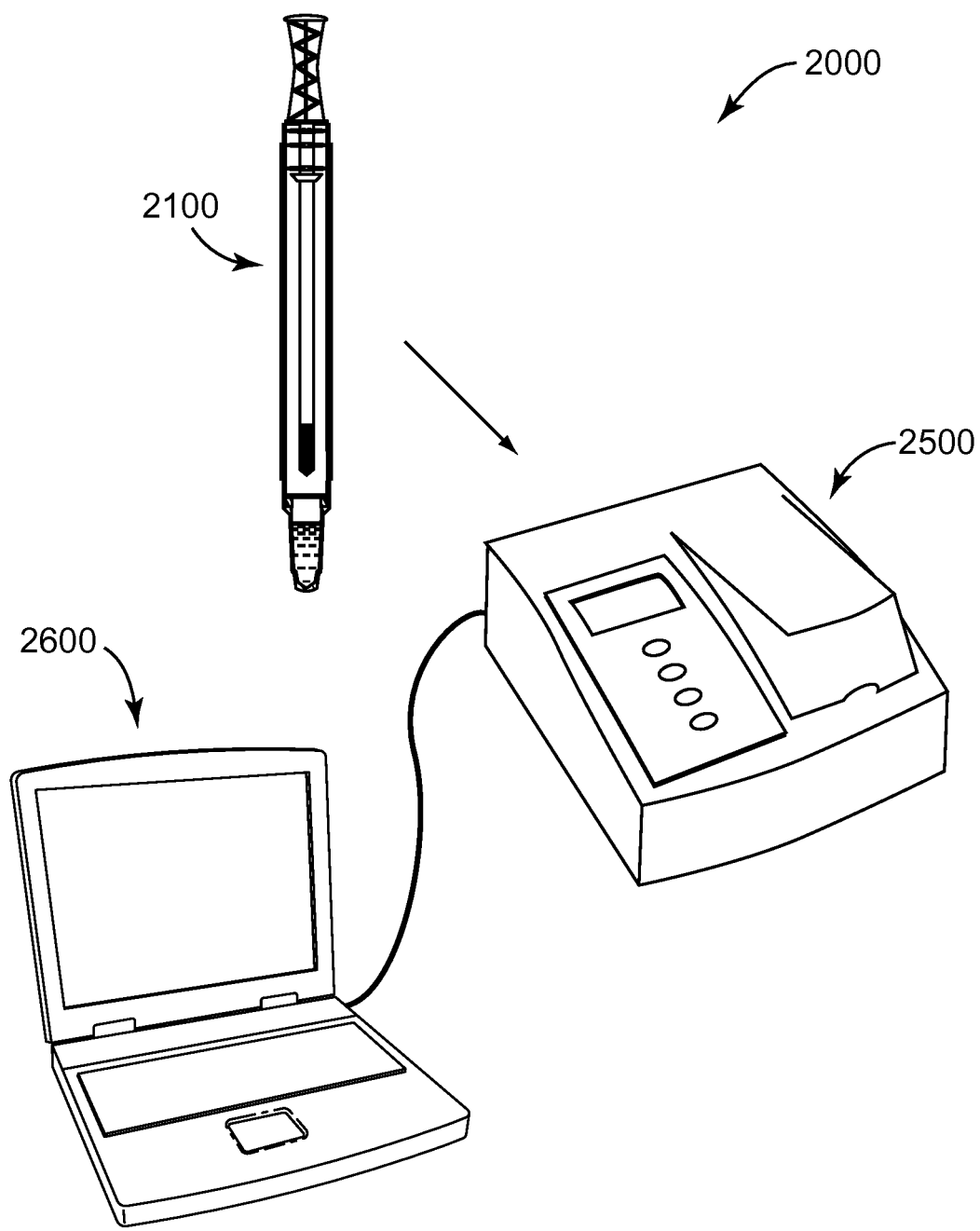
FIG. 9 is a schematic view of a system for assessing the efficacy of a washing process according to the present disclosure.

In another aspect, the present disclosure provides a system. The system can be used to test the efficacy of a washing process. The system comprises a monitoring device comprising a container and a test element according to any embodiment described herein. The test element comprises a predetermined quantity of a tracer analyte releasably adhered thereto. The system further comprises an analytical instrument capable of detecting a detectable product that indicates a presence and, optionally, a quantity of tracer analyte in one or more chemical reaction. In some embodiments, the system may further comprise a computer capable of receiving data from the analytical instrument and a memory (not shown) capable of storing the received data. In any embodiment, the system further comprises the process challenge device disclosed herein. FIG. 9 shows a schematic view of one embodiment of a system 2000 according to the present disclosure. The system comprises a monitoring device 2100 and an analytical instrument 2500. Optionally, the system 2000 further comprises a computer 2600.

Optionally, the computer 2600 may comprise software or firmware capable of operating the analytical instrument 2500. In any embodiment, the software may be adapted to facilitate the detection of the detectable product that indicates a presence of the tracer analyte. The computer 2600 may include memory and may create an information database in its memory to track and store such information. Computer 2600 may associate various types of information with the monitoring device 2100. Numerical values associated with one or more test elements may be analyzed and/or stored by computer 2600. In addition, a numerical value associated with a first test element can be analyzed by computer 2600 to compare the value to second test element and/or a control value associated with a standard (e.g., a positive control, a negative control).

Computer 2600 may include a microprocessor that executes software for analysis of monitoring device 2100, and for database management consistent with the techniques known in the art. Accordingly, computer 2600 may also include memory to store the various types of information associated with a particular monitoring device 2100. Computer 2600 may comprise a personal computer (PC), desktop computer, laptop computer, handheld computer, workstation, or the like.

In another aspect, the present disclosure provides a homogeneous, dried artificial test soil. The test soil is a composition comprising a target analyte (e.g., an acid, a base, a nucleotide, a protein, a nucleic acid, a carbohydrate, or hemoglobin) according to the present disclosure. In a preferred embodiment, the target analyte is Adenosine-5'-triphosphate. In any embodiment, the test soil composition further can comprise an optional dye in an amount sufficient to be optically detectable, as described herein. The test soil further comprises a polymeric binder. The dried test soil is prepared by dissolving and/or making a homogeneous dispersion of the target analyte, polymeric binder, and optional dye in a suitable solvent (e.g., water, alcohol, or mixtures thereof), applying the mixture to a surface (e.g., by spraying, dip-coating, or other coating processes known in the art) of a substrate, and removing at least a portion of the solvent (e.g., substantially all of the solvent) to obtain a dried coating on the substrate.

Without being bound by theory, the polymeric binder provides one or more of the following technical effects in the test soil composition: 1) the polymeric binder provides bulk mass that can facilitate the adherence of relatively small quantities of tracer analyte to a substrate, 2) the polymeric binder provides adhesive properties to facilitate the adherence of the test soil composition to the substrate, 3) the polymeric binder provides a solubility and/or diffusion barrier that prevents the substantially immediate dissolution and release of the tracer analyte from the substrate when the test soil is contacted with a solvent (e.g., water, hot water) in which it is soluble or dispersible and, 4) in the instance where the polymeric binder comprises a protein, the polymeric binder may provide some buffering capacity to maintain the pH of the composition.

Suitable polymeric binders include, for example, polyols (e.g., polyvinyl alcohol, polysaccharides), polyethers (e.g., polyethylene oxides), and polyamides (e.g., proteins such as serum albumin, for example). The molecular weight of the polymeric binder can be selected such that the binder is more or less soluble in the liquid used in the washing process. For a given coating weight, higher molecular weight binders may be used to produce test soil compositions that are more difficult to wash off. Conversely, for a given coating weight, lower molecular weight binders may be used to produce test soil compositions that are less difficult to wash off.

Embodiments

Embodiment A is a monitoring device, comprising:
a test composition comprising a predetermined quantity of tracer analyte;
a test element comprising a test portion to which the test composition is releasable adhered;
a detection reagent; and
a container comprising a first end with an opening and a second end opposite the first end;
wherein the container is configured to receive the test portion and configured to be operationally coupled to an analytical instrument;
wherein the tracer analyte and the detection reagent are capable of participating in one or more chemical reaction that results in the formation of a detectable product.

Embodiment B is the monitoring device of Embodiment A, wherein the test portion comprises at least one recessed area, wherein the test composition is adhered in the recessed area.

Embodiment C is the monitoring device of any one of the preceding Embodiments, wherein the test composition further comprises a polymeric binder.

Embodiment D is the monitoring device of any one of the preceding Embodiments, wherein the tracer analyte is selected from the group consisting of a plurality of viable microorganisms or a biomolecule associated therewith, an acid, a base, a nucleotide, a protein, a nucleic acid, a carbohydrate, or hemoglobin.

Embodiment E is the monitoring device of Embodiment D, wherein the plurality of viable microorganisms comprises a yeast microorganism.

Embodiment F is the monitoring device of Embodiment D or Embodiment E, wherein the test portion comprises a porous fibrous nonwoven matrix, wherein the plurality of viable microorganisms is disposed on or in the fibrous nonwoven matrix.

Embodiment G is the monitoring device of Embodiment F, wherein the test portion further comprises a plurality of inorganic particles dispersed in the fibrous nonwoven matrix, wherein plurality of viable microorganisms is releasably adhered to two or more of the plurality of inorganic particles.

Embodiment H is the monitoring device of any one of the preceding Embodiments, further comprising a frangible seal, wherein a receiving chamber is disposed on a first side of the frangible seal proximate the opening and a cuvette chamber is disposed on a second side of the frangible seal distal the opening.

Embodiment I is the monitoring device of Embodiment H, wherein the test element is configured to disrupt the frangible seal.

Embodiment J is the monitoring device of any one of the preceding Embodiments, wherein the container includes a first solvent disposed therein.

Embodiment K is the monitoring device of Embodiment J, wherein the tracer analyte is soluble in the solvent.

Embodiment L is the monitoring device of Embodiment J or Embodiment K, wherein the test composition is dispersible in the solvent.

Embodiment M is the monitoring device of any one of the Embodiments J through L as dependent on Embodiment H, wherein the solvent is disposed in the cuvette chamber.

Embodiment N is the monitoring device of Embodiment M, wherein the detection reagent is disposed in the container.

Embodiment O is the monitoring device of Embodiment N, wherein the detection reagent is disposed in the receiving chamber or the cuvette chamber.

Embodiment P is the monitoring device of any one of the preceding Embodiments, wherein the test element further comprises a reservoir with a second solvent disposed therein, a hollow stem, and a liquid flow regulator capable of placing the reservoir in fluid communication with the hollow stem.

Embodiment Q is the monitoring device of Embodiment P, wherein the tracer analyte is soluble in the second solvent.

Embodiment R is the monitoring device of Embodiment P or Embodiment Q, wherein the test composition is dispersible in the second solvent.

Embodiment S is the monitoring device of any one of Embodiments P through R, wherein the detection reagent is disposed in the reservoir.

Embodiment T is the monitoring device of any one of the preceding Embodiments, wherein the container comprises a cuvette portion configured to be operationally coupled with the analytical instrument.

Embodiment U is the monitoring device of any one of Embodiments A through T, further comprising a secural element.

Embodiment V is a method of assessing the efficacy of a washing process, comprising:
exposing the test portion of a monitoring device according to any one of Embodiments A through U to the washing process;
after exposing the test portion to the washing process, contacting the test portion with the detection reagent in the container; and
using the analytical instrument to detect a presence or an absence of the detectable product;

wherein the presence of the detectable product indicates a presence of tracer analyte on the test portion after exposing the test portion to the washing process.

Embodiment W is the method of Embodiment V, wherein exposing the test portion to the washing process comprises placing the test portion into an automated washer and performing at least a portion of an automated wash cycle while the test portion is disposed in the automated washer.

Embodiment X is the method of Embodiment W, wherein the automated washer comprises an automated washer-disinfector.

Embodiment Y is the method of any one of Embodiments V through X, wherein using the analytical instrument to detect a presence or an absence of the detectable product comprises using the analytical instrument to measure a quantity of the tracer analyte.

Embodiment Z is method of any one of Embodiments W through Y, wherein exposing the test portion of a monitoring device comprises exposing the test portion of a plurality of monitoring devices, wherein the method further comprises positioning a first monitoring device at a first predefined location in the automated washer and positioning a second monitoring device at a second predefined location in the automated washer.

Embodiment AA is the method of Embodiment Z, as dependent upon Embodiment Y, further comprising the step of comparing a measured quantity of tracer analyte associated with the first monitoring device to a measured quantity of tracer analyte associated with the second monitoring device.

Embodiment BB is the method of any one of Embodiments Y through AA, further comprising comparing the measured quantity of the tracer analyte to a predefined standard.

Embodiment CC is the method of any one of Embodiments Y through BB, further comprising using the at least one measured quantity to define an action limit.

Embodiment DD is the method of any one of Embodiments Y through BB, further comprising comparing the measured quantity to a predefined action limit.

Embodiment EE is the method of any one of Embodiments V through DD, further comprising associating a first datum related to a quantity of tracer analyte detected in a sample with a second datum related to other information related to the sample and electronically storing the associated first and second data.

Embodiment FF is the method of Embodiment EE, wherein the second datum comprises information selected from the group consisting of a date, a time, a washing apparatus, an operator, an instrument to be washed, and a combination of two or more of any of the foregoing test data.

Embodiment GG is the method of any one of Embodiments V through FF, further comprising the step of placing the test portion of the monitoring device in a receiver configured to restrict fluidic accessibility to the test portion.

Embodiment HH is the method of Embodiment GG, wherein placing the test portion of the monitoring device in a receiver configured to restrict fluidic accessibility to the test portion comprises placing the test portion into an interior space of a lumened object.

Embodiment II is the method of any one of Embodiments V through HH further comprising, before exposing the test portion of the monitoring device to the washing process, positioning at least a part of the test portion of the monitoring device in a process challenge device.

Embodiment JJ is a method of processing an object to be decontaminated, comprising:
processing as a single batch in a decontamination process:
an object having an unknown amount of biological soil disposed thereon and/or therein;
a monitoring device comprising a predetermined quantity of tracer analyte according to any one of Embodiments A-U;
after exposing the test portion to the decontamination process, contacting the test portion with the detection reagent in the container; and
using the analytical instrument to detect a presence or an absence of the detectable product;
wherein the presence of the detectable product indicates a presence of the tracer analyte on the test portion after exposing the test portion to the washing process.

Embodiment KK is the method of Embodiment JJ, wherein processing the object and the monitoring device in a decontamination process comprises processing the object and the monitoring device in an automated washer or an automated washer-disinfector.

Embodiment LL is the method of Embodiment JJ or KK, wherein processing as a single batch in a decontamination process the object and the monitoring device comprises processing as a single batch in a decontamination process the object and a plurality of the monitoring devices.

Embodiment MM is the method of Embodiment LL, wherein processing a plurality of monitoring devices comprises processing a first monitoring device at a first location and processing a second monitoring device at a second location that is spaced apart from the first location.

Embodiment NN is the method of Embodiment MM as dependent on KK, wherein processing a plurality of monitoring devices comprises processing the plurality of monitoring devices in an automated washer or an automated washer-disinfector.

Embodiment OO is the method of any one of Embodiments JJ through NN, wherein detecting a presence or an absence of the detectable product further comprises calculating a quantity of tracer analyte remaining on the test portion after exposing the test portion to the decontamination process.

Embodiment PP is the method of Embodiment OO, further comprising comparing the quantity of tracer analyte remaining on the test portion of at least one monitoring device after exposing the test portion to the decontamination process to a predetermined quantity of tracer analyte associated with an action limit.

Embodiment QQ is the method of Embodiment PP, further comprising releasing the object for use in a first subsequent process if the quantity of tracer analyte remaining on the test portion of the at least one monitoring device after exposing the test portion to the decontamination process is less than or equal to the predetermined quantity.

Embodiment RR is the method of Embodiment PP, further comprising releasing the object for use in a second subsequent process if the quantity of tracer analyte remaining on the test portion of the at least one monitoring device after exposing the test portion to the decontamination process is greater than or equal to the predetermined quantity.

Embodiment SS is the method of any one of Embodiments JJ through RR, wherein calculating a quantity of tracer analyte remaining on the test portion comprises quantifying ATP, a blood component, or a protein.

Embodiment TT is a kit, comprising:
a container comprising a first end with an opening and a second end opposite the first end, wherein the container includes a detection reagent disposed therein; and a test element comprising a test portion to which a test composition is releasably adhered, wherein the test composition comprises a predetermined quantity of tracer analyte;

wherein the container is configured to receive the test portion and configured to be operationally coupled to an analytical instrument;

wherein the tracer analyte and the detection reagent each are capable of participating in one or more chemical reaction that results in the formation of a detectable product.

Embodiment UU is kit of Embodiment TT, wherein the container further comprises a solvent disposed therein.

Embodiment VV is the kit of Embodiment TT or Embodiment UU, wherein the test element further comprises a reservoir with a solvent disposed therein, wherein the test element comprises a hollow stem and the reservoir comprises a liquid flow regulator capable of placing the reservoir in fluid communication with the hollow stem.

Embodiment WW is the kit of any one of Embodiment TT through VV, further comprising a means to secure a test element.

Embodiment XX is the kit of any one of Embodiments TT through WW, further comprising an article comprising a receiver configured to restrict fluidic accessibility to the test portion.

Embodiment YY is the kit of Embodiment XX, wherein the article is a lumened object.

Embodiment ZZ is the kit of any one of Embodiments TT through YY, wherein the tracer analyte is selected from the group consisting of a plurality of viable microorganisms, an acid, a base, a nucleotide, a protein, a nucleic acid, a carbohydrate, or hemoglobin.

Embodiment AAA is the kit of Embodiment ZZ, wherein the test portion comprises a fibrous nonwoven matrix, wherein the plurality of viable microorganisms is disposed on or in the fibrous nonwoven matrix.

Embodiment BBB is the kit of Embodiment AAA, wherein the test portion further comprises a plurality of inorganic particles dispersed in the fibrous nonwoven matrix, wherein the plurality of viable microorganisms is releasably adhered to two or more of the plurality of inorganic particles.

Embodiment CCC is a system for testing the efficacy of a washing process, comprising:

a monitoring device comprising a container and a test element that includes a test portion to which a test composition comprising a predetermined quantity of a tracer analyte is releasably adhered according to any one of Embodiments A through U; and an analytical instrument capable of detecting the detectable product;

wherein the container is configured to receive the test portion and configured to be operationally coupled to the analytical instrument.

Embodiment DDD is the system of Embodiment CCC, further comprising a computer capable of receiving data from the analytical instrument and a memory capable of storing the received data.

Embodiment EEE is the system of Embodiment CCC or Embodiment DDD, further comprising a process challenge device capable of receiving at least a part of the test portion of the test element.

Embodiment FFF is an article comprising a homogeneous dried composition removably adhered thereto, wherein the composition comprises a predetermined amount of adenosine-5'-triphosphate and a dye in an amount sufficient to be optically detectable.

Embodiment GGG is the article of Embodiment FFF, wherein the composition further comprises a polymeric binder.

Embodiment HHH is the article of Embodiment GGG, wherein the polymeric binder comprises a water-dispersible polymeric binder.

Embodiment III is the article of Embodiment GGG or Embodiment HHH, wherein the polymeric binder comprises polyvinyl alcohol, polyethylene glycol, or mixtures thereof.

Embodiment JJJ is a homogeneous, dried artificial test soil consisting essentially of adenosine-5'-triphosphate, or a salt thereof, and a polymeric binder.

Embodiment KKK is the test soil of Embodiment JJJ, wherein the polymeric binder comprises polyvinyl alcohol, polyethylene glycol, or mixtures thereof.

Embodiment LLL is the test soil of Embodiment JJJ or Embodiment KKK, wherein the polymeric binder comprises a water-dispersible polymeric binder.

Objects and advantages of this invention are further illustrated by the following examples, but the particular materials and amounts thereof recited in these examples, as well as other conditions and details, should not be construed to unduly limit this invention.

EXAMPLES

Unless stated otherwise, all reagents used in the following examples were reagent-grade. 3M CLEAN-TRACE Water Test (Total ATP) test units, 3M CLEAN-TRACE Water Test (Free ATP) test units, and the 3M CLEAN-TRACE NG Luminometer were obtained from 3M Company (St. Paul, Minn.).

Preparative Example 1

Preparation of Tracer Analyte-Coated Test Elements

A dilute suspension of porcine red blood cells (Solution I) was prepared by mixing 50 milliliters of porcine blood in 0.4% (w/v) sodium citrate (obtained from Cocalico Biological, Inc.; Reamstown, Pa.) with 50 milliliters of 0.9% (w/v) sodium chloride. A solution (Solution II) of 250 mM calcium chloride was prepared by dissolving 1.387 g of $CaCl_2$ in distilled water. A coating solution (Solution III) was prepared by mixing 20 milliliters of Solution I with 0.2 milliliters of Solution II. Solution III was used to coat sample acquisition devices less than 15 minutes after it was prepared because the addition of the calcium chloride caused the blood to clot.

The sample-acquiring tips of five 3M CLEAN-TRACE Water Test (Total ATP) sample acquisition devices (Set A) were dipped into Solution III and immediately withdrawn from the coating solution. In addition, the sample-acquiring tips of five 3M CLEAN-TRACE Water Test (Free ATP) sample acquisition devices (Set B) were dipped into Solution III and immediately withdrawn from the coating solution. All coated sample acquisition devices (hereinafter, "test elements") were inverted and the handles were placed into a microcentrifuge rack. The test elements were allowed to dry in a biosafety hood at ambient temperature and humidity for 2.5 hours. After drying, the test elements were returned to their respective ATP test units.

Preparative Example 2

Preparation of Corona-Treated, Tracer Analyte-Coated Test Elements

In order to increase the hydrophilicity of the coated portion of the test elements, representative sets of sample acquisition devices were subjected to corona plasma treatment before dipping each of them into a blood-containing solution and drying them as described in Preparative Example 1.

3M CLEAN-TRACE Water Test (Total ATP) sample acquisition devices (Set C) were surface-treated using a corona plasma process. The devices were held by the handle and the tips were positioned about 1.4 mm away from a hand-held corona plasma source (model BD-20AC corona plasma source obtained from Electro-Technic Products, Inc.; Chicago, Ill.). The devices were slowly rotated about their respective longitudinal axis for about 1 minute, thereby exposing the entire circumference of the tip to the corona plasma field. The devices were subsequently dipped into Solution III and dried as described in Preparative Example 1.

Preparative Example 3

Preparation of Diamond-Like Glass-Coated, Tracer Analyte-Coated Test Elements

In order to increase the hydrophilicity of the coated portion of the test elements, representative sets of sample acquisition devices were coated with diamond-like glass before dipping each of them into a blood-containing solution and drying them as described in Preparative Example 1.

3M CLEAN-TRACE Water Test (Total ATP) sample acquisition devices (Set D) were coated with a diamond-like glass coating according to the following process. The diamond-like glass film was deposited in a commercial batch reactor (Plasmatherm Model 3032), which was configured for reactive ion etching (RIE) with a 69 cm lower powered electrode and central gas pumping. The chamber was pumped by a roots blower (Edwards Model EH1200) backed by a dry mechanical pump (Edwards Model iQDP80). RF power was delivered by a 5 kW, 13.56 Mhz solid-state generator (RFPP Model RF30S through an impedance matching network. The system had a nominal base pressure of 0.667 Pascal. The flow rates of the gases were controlled by mass flow controllers (MKS Instruments, Inc.). Substrates for deposition were placed on the lower powered electrode. The samples were then plasma treated in the following manner. The samples were placed on the powered electrode of the batch plasma apparatus. The plasma treatment was done in a series of treatment steps. First, the tips were treated with oxygen plasma by flowing oxygen gas at a flow rate of 500 standard cm3/min and plasma power of 300 watts for 20 seconds. After the oxygen plasma treatment, a diamond-like glass film was deposited by flowing tetramethylsilane gas at a flow rate of 150 standard cm3/min, and plasma power of 300 watts for 20 seconds. The diamond-like glass film was further surface modified by treating in oxygen plasma at a flow rate of 500 cm3/min and plasma power of 300 watts for 60 seconds. After the plasma deposition was completed, the chamber was vented to atmosphere and the samples were removed.

The devices were subsequently dipped into Solution III and dried as described in Preparative Example 1.

Preparative Example 4

Preparation of Surface-Treated, Tracer Analyte-Coated Test Elements

3M CLEAN-TRACE Water Test (Total ATP) sample acquisition devices (Set G) were surface-treated using a corona plasma process similar to that described in Preparative Example 2 except the sample acquisition devices were rotated in the corona plasma for an additional 30 seconds. The devices were subsequently dipped into Solution III and dried as described in Preparative Example 1.

Preparative Examples 5-7 and 5a-7a

Preparation of Test Compositions Comprising Adenosine-5'-triphosphate and a Polymeric Binder CELVOL-brand polyvinyl alcohol polymers were obtained from Sekisui Specialty Chemicals (Secaucus, N.J.). A stock solution (1 mg/mL) of ATP was prepared in sterile deionized water. The stock solution was serially diluted in sterile deionized water to produce one working solution ("A") containing 1 microgram/mL ATP and another working solution ("B") containing 0.7 micrograms/mL ATP, respectively. For Preparative Examples 5-7, aliquots of working solution "A" were added to individual mixing jars. For Preparative Examples 5a-7a, aliquots of working solution "B" were added to individual mixing jars. A solution of FD&C Red Dye #40 was prepared by dissolving 160 mg of F&DC Red Dye #40 into 40 mL of sterile water. The 4 mg/mL Red Dye #40 solution was added to each of the jars with the ATP working solution and the jars were placed in a water bath at 80° C. The appropriate amount of a designated polymeric binder (reported in each particular Example, below) was added to each jar at a rate of about 1.0 gram/minute with stirring to obtain the reported concentration of binder. Each mixture was stirred for about one hour to allow the polymeric binder to fully dissolve. The final concentration of ATP for each Preparative Example 5-7 was 1 microgram/mL. The final concentration of Red Dye #40 was 0.13 mg/mL, which was added primarily for visibility when coating the device tips.

TABLE 1

Composition of Artificial Test Soils comprising ATP and a polymeric binder.

| Preparative Example | Polymeric Binder | ATP Concentration |
|---|---|---|
| 5 | Polyvinyl alcohol (CELVOL 425) | 1.0 microgram/mL |
| 5a | Polyvinyl alcohol (CELVOL 425) | 0.7 microgram/mL |
| 6 | Polyvinyl alcohol (CELVOL 443) | 1.0 microgram/mL |
| 6a | Polyvinyl alcohol (CELVOL 443) | 0.7 microgram/mL |
| 7 | Polyethylene glycol (8000) | 1.0 microgram/mL |
| 7a | Polyethylene glycol (8000) | 0.7 microgram/mL |

Preparative Example 8

Preparation of Artificial Test Soils (ATSs) Comprising Adenosine-5'-triphosphate A commercially available dehydrated artificial test soil with the product name WASHER DISINFECTOR SOIL TEST (Order Code 2304), used for Preparative Example 8 was obtained from Albert Browne International Ltd (Leicester, UK). The artificial test soil was rehydrated using a sterile water solution containing 1 microgram/mL ATP that was made as described in Preparative Examples 5-7.

Example 1

Measurement of ATP from Blood-Coated Test Elements

The amount of ATP from the blood coated on each test element made according to Preparative Example 1 was measured in a bioluminescent (i.e., luciferin/luciferase reaction) assay using a 3M CLEAN-TRACE NG Luminometer. At least portions of the coating were observed to crack and separate from the test elements after drying. Table 2 shows the ATP measurement results from each set.

TABLE 2

Amount of ATP detected from blood-coated test elements.
All results are reported in Relative Light Units (RLU).

| | Test Element | |
|---|---|---|
| | Set A (Total ATP) (n = 4) | Set B (Free ATP) (n = 5) |
| Average | 1,104,693 | 1,097,112 |
| STDEV | +/−29,179 | +/−14,710 |

Example 2

Measurement of ATP from Surface-Treated, Blood-Coated Test Elements

3M CLEAN-TRACE Water Test (Total ATP) sample acquisition devices (Set D) were surface-treated using a diamond-like glass (DLG) coating process. The devices were coated with DLG using the method described above. After the devices were coated with the DLG, they were dipped in Solution III and dried as described in Preparative Example 1.

3M CLEAN-TRACE Water Test (Total ATP) sample acquisition devices (Set E) did not receive any surface treatment. They were dipped in Solution III and dried as described in Preparative Example 1.

A 3M CLEAN-TRACE Water Test (Total ATP) sample acquisition device (Set F) did not receive any surface treatment. The device was dipped in Solution I (Example 1) and dried according to the process described in Preparative Example 1.

The blood-coated devices (i.e., test elements) were returned to their respective ATP test units and the amount of ATP from the blood coated on each test element was measured in a bioluminescent (i.e., luciferin/luciferase reaction) assay using a 3M CLEAN-TRACE NG Luminometer. Table 3 shows the ATP measurement results from each set. It was noted that, although some flaking of the dried coating occurred on test elements from Set C and Set D, it was significantly less than set E. indicating the coating was retained better by the surface-modified test elements than by the test elements that were not surface-treated.

TABLE 3

Amount of ATP detected from blood-coated test elements.
All results are reported in Relative Light Units (RLU).
The number shown in parentheses is the number of test elements that was tested for each particular set.

| | Test Element | | | |
|---|---|---|---|---|
| | Set C (n = 3) Plasma Corona Treated Dipped in Soln. III | Set D (n = 4) DLG Coated Dipped in Soln. III | Set E (n = 2) Untreated Soln. III | Set F (n = 1) Untreated Soln. I |
| Average | 1,150,369 | 1,108,209 | 1,145,357 | 1,153,984 |
| STDEV | +/−10965 | +/−71931 | +/−18705 | (n = 1) |

Example 3

The Use of Test Elements to Monitor the Efficacy of a Defective Washing Process

Test elements made according to Preparative Example 3 were placed into stainless steel wire mesh baskets (approximate size 50 cm long×20 cm wide×10 cm tall) that are used to hold articles to be washed in a GETINGE 46-4 model-washer disinfector (Getinge USA, Inc., Rochester, N.Y.). All test elements of Sets C and D were securely fastened to the inside corners of the baskets using hose clamps and zip ties. The test elements of Set E were placed at one end inside each basket. The baskets were then placed into the GETINGE 46-4 instrument washer. Two baskets were placed in each of the three levels available in the GETINGE 46-4 instrument washer. A "defective" washer-disinfector cycle was run. The defective cycle included a shortened hot-water (60° C.) wash, did not include use of a detergent, and did not include a very-hot (90° C.) final rinse. The parameters for this defective wash cycle ("Incomplete Cycle I") are listed in Table 4. The conditions of the wash cycle were not sufficient to comply with most existing standards for washing medical instruments in a hospital. After completion of the wash cycle and prior to the measuring the blood (ATP) retained on each test element, residual water from the wash cycle was removed from each tip of test elements in a first group (Group A), by gently shaking the test element 2 or 3 times. The other test elements (Group B) were not shaken prior to ATP measurement. The washed test elements were returned to their respective ATP test units and the amount of ATP from the blood coated on each test element was measured in a bioluminescent (i.e., luciferin/luciferase reaction) assay using a 3M CLEAN-TRACE NG Luminometer. Table 5 shows the ATP measurement results from each set.

TABLE 4

Washing, rinsing, and drying parameters for Incomplete Cycle I.

| Length | Process Step |
|---|---|
| 1.0 min. | Cold-water pre-rinse |
| 3.0 min. | Hot-water (60° C.) wash |
| 1.0 min. | Hot-water (60° C.) first rinse |
| 1.0 min. | Hot-water (60° C.) second rinse |
| 10.0 min. | Dry |

TABLE 5

Amount of ATP detected from blood-coated test elements. All results are reported in Relative Light Units (RLU). Negative Control devices that were not surface-modified and were not dipped in swine blood had readings of 4 RLU to 12 RLU (data not shown in table).

| | Set C Plasma Corona Treated Dipped in Soln. III | Set D DLG Treated Dipped in Soln. III | Set E Untreated Dipped in Soln. III |
|---|---|---|---|
| Group A (shaken) | 570 | 327 | 122 |
| | 49 | 255 | |
| Group B (not shaken) | 99 | 490 | 67 |
| | 808 | 436 | |
| Average | 382 | 377 | 95 |
| STDEV | +/−369 | +/−106 | 39 |

Example 4

The Use of Test Elements to Monitor the Efficacy of a Nondefective Washing Process Test elements made according to Preparative Example 4 (Set G) and Set E (described above) were placed into stainless steel wire mesh baskets that are used to hold articles to be washed in a GETINGE 46-4 model washer disinfector (Getinge USA, Inc., Rochester, N.Y.). All test elements of Set G were securely fastened to the inside corners of the baskets using hose clamps and zip ties. The test elements of Set E were likewise secured at one end inside each basket. Additionally a set of negative controls were placed loosely on the bottom of each basket. These negative control devices were not surface-modified and were not dipped in swine blood. The baskets were then placed into the GETINGE 46-4 instrument washer. A "nondefective" washer-disinfector cycle was run. The nondefective cycle included a longer hot-water (60° C.) wash than the "defective cycle, it include use of a multi-enzyme detergent (BMEC 70508-A detergent available from 3M Company, St. Paul, Minn.), and it included a very-hot (90° C.) final rinse. The parameters for this nondefective wash cycle ("Complete Cycle II") are listed in Table 6. The conditions of the wash cycle were sufficient to comply with most existing standards for washing medical instruments in a hospital. After completion of the wash cycle and prior to the measuring the blood (ATP) retained on each test element, residual water from the wash cycle was removed from each tip of test elements by gently shaking the test element 2 or 3 times. The washed test elements were returned to their respective ATP test units and the amount of ATP from the blood coated on each test element was measured in a bioluminescent (i.e., luciferin/luciferase reaction) assay using a 3M CLEAN-TRACE NG Luminometer. Table 7 shows the ATP measurement results from each set.

TABLE 6

Washing, rinsing, and drying parameters for Complete Cycle II.

| Length | Process Step |
| --- | --- |
| 1.0 min. | Cold-water pre-rinse |
| 5.0 min. | Hot-water (60° C.) wash with detergent |
| 1.0 min. | Hot-water (60° C.) first rinse |
| 1.0 min. | Hot-water (60° C.) second rinse |
| 1.0 min. | Very-hot (90° C.) final rinse |
| 10.0 min. | Dry |

TABLE 7

Amount of ATP detected from blood-coated test elements. All results are reported in Relative Light Units (RLU). The number shown in parentheses is the number of test elements that was tested for each particular set. Negative Control devices were not surface-modified and were not dipped in swine blood.

| | Set G<br>Plasma Corona<br>Treated Dipped in<br>Soln. III<br>(n = 8) | Set E<br>Untreated<br>Dipped in<br>Soln. III<br>(n = 3) | Negative Control<br>Untreated<br>No Soil<br>(n = 4) |
| --- | --- | --- | --- |
| Average | 16 | 7 | 8 |
| STDEV | +/−6 | +/−1 | +/−3 |

The corona-treated test devices from Set G that were exposed to the Complete Cycle II shown in Table 7, all showed lower levels of ATP than the corresponding test devices that were exposed to the Incomplete Cycle I (see Table 5). In addition, the ATP levels measured from blood-coated, corona-treated test devices exposed to Complete Cycle II were only slightly higher than the negative control test devices, which were not coated with swine blood.

Example 5

Measurement of ATP from Surface-Treated Test Elements with CELVOL Polymeric Binder CLEAN-TRACE Water Test (Total ATP) test units were plasma corona treated as described above for 90 seconds. The devices were subsequently dipped into Preparative Example 5a (CELVOL 425), to create Set H. Other plasma corona treated devices were subsequently dipped into Preparative Example 6a (CELVOL 443), to create Set I. After dipping, test devices of Set H and Set I were rotated slowly on top of a small piece of PARAFILM to remove excess material of the ATP spiked binder coating from the tip of the test device. The test devices were dried for 1 hour at 60 degrees C., then shaken by hand for 45 seconds, and then to returned to their respective ATP test units and the amount of ATP on each test element was measured in a bioluminescent (i.e., luciferin/luciferase reaction) assay using a 3M CLEAN-TRACE NG Luminometer. Table 8 shows the ATP measurement results from each set. Additionally, for comparison, 3 test devices for Set H were also assessed for ATP without drying, in a "wet" condition.

TABLE 8

Amount of ATP detected from CELVOL Polymeric Binder coated test elements. All results are reported in Relative Light Units (RLU). The number shown in parentheses is the number of test elements that was tested for each particular set.

| | Set H<br>13.0 wt. %<br>CELVOL 425<br>Wet (not dried)<br>(n = 3) | Set H<br>13.0 wt. %<br>CELVOL 425<br>Dried 1 hour<br>(n = 3) | Set I<br>14.9 wt. %<br>CELVOL 443<br>Dried 1 hour<br>(n = 3) |
| --- | --- | --- | --- |
| Average | 611,736 | 412,296 | 402,364 |
| STDEV | +/−49,332 | +/−30,452 | +/−60,943 |

Example 6

Measurement of ATP from Surface-Treated Test Elements with ATP Spiked Coatings after Wash Disinfection Cycle CLEAN-TRACE Water Test (Total ATP) test units were plasma corona treated as describe above for 90 seconds. The devices were subsequently dipped into the following Preparative Examples containing ATP: Preparative Example 6a (CELVOL 443), to create Set J, or dipped in Preparative Example 7a (PEG) to create Set K or dipped in Preparative Example 8 (commercially available artificial test soil), to create Set L. The concentration of the binder portion of Preparative Examples 6 and 7 are described in Table 8, below. After dipping, test devices of Sets J, K and L were brushed with a small commercially available acid brush in a direction parallel to the major axis of the test device, which is a direction orthogonal to the recessed grooves of the test device. This brushing physically removed the excess material of the ATP spiked coating from the tip of the test device, leaving the majority of the coated material remaining within the recessed grooves of the test device tip. The test devices were dried for 1 hour at 60° C., and then shaken by hand for 45 seconds. Each of Set J, K and L were divided into 3 sub-groups. The 3 sub-groups were subjected to one of (1) "No Wash" or (2) the defective wash cycle "Incomplete Cycle I" described in Table 4, or (3) the nondefective wash cycle, "Complete Cycle II" described in Table 6. Each sub-group under each wash condition, including a set of uncoated test devices as controls, consisted of 5 individual test devices (n=5). The monitoring devices that were to be subjected to wash cycles were placed loosely in the corner of the stainless steel wire mesh baskets that are used to hold articles to be washed in a GETINGE 46-4 model washer disinfector, used in Example 4. Afterwards the monitoring devices were then to returned to their respective ATP test units and the amount of ATP on each test element was measured in a bioluminescent (i.e., luciferin/luciferase reaction) assay using a 3M CLEAN-TRACE NG Luminometer. Table 9 shows the ATP measurement results from each J, K and L set and sub-group.

TABLE 9

Amount of ATP detected from coated test elements. All results are reported in Relative Light Units (RLU). Negative Control devices were not surface-modified and were not coated.

| Conditions | Set J 9.1 wt. % CELVOL 433 (n = 5) | Set K 50.0 wt. % PEG (n = 5) | Set L ATS (n = 5) | Negative Controls Uncoated Test Units (n = 5) |
|---|---|---|---|---|
| No Wash Average | 560,327 | 557,192 | 16,852 | 182 |
| No Wash STDEV | +/−10,104 | +/−48,598 | +/−2,159 | +/−294 |
| Cycle I Average | 3,088 | 949 | 1,515 | 52 |
| Cycle I STDEV | +/−3,589 | +/−1,715 | +/−3,235 | +/−8 |
| Cycle II Average | 527 | 34 | 107 | 24 |
| Cycle II STDEV | +/−1,110 | +/−18 | +/−191 | +/−28 |

Example 7

Measurement of ATP from Surface-Treated Test Elements with ATP Spiked Coatings after Extended Storage and Wash Disinfection Cycles Monitoring devices were prepared as in Example 6, Set J, dipped into Preparative Example 6a (CELVOL 443, and brushing with the acid brush, to create Set M. However, additionally for Set M, the test devices were dipped and brushed a total of four times (4 coatings). The intermittent drying time was 40 minutes in a 60° C. oven, followed by a final dry time of 1 hour at 60° C. The concentration of the CELVOL 443 portion of Preparative Example 6a used for Set M was 9.2 wt. %. Set M was divided into sub-groups that were stored under ambient conditions for various lengths of time (0, 7, 14 days) to evaluate the stability over time of the coated monitoring devices prior to use. Negative Controls (untreated and uncoated test devices) were stored under like conditions over the same time periods. Also like Example 6, the sub-groups of Set M were also subjected to one of (1) "No Wash" or (2) the defective wash cycle "Incomplete Cycle I" described in Table 4, or (3) the nondefective wash cycle, "Complete Cycle II" described in Table 6. The test devices that were to be subjected to wash cycles were placed loosely in the corner of the stainless steel wire mesh baskets that are used to hold articles to be washed in a GETINGE 46-4 model washer disinfector, used in Example 4. Afterwards the devices were then to returned to their respective ATP test units and the amount of ATP on each test element was measured in a bioluminescent (i.e., luciferin/luciferase reaction) assay using a 3M CLEAN-TRACE NG Luminometer. Table 10 shows the ATP measurement results from Set M.

TABLE 10

Amount of ATP detected from 4X coated test elements after storage. All results are reported in Relative Light Units (RLU). Negative Control devices were not surface-modified and were not coated.

| Conditions | Set M Day 0 (n = 4) | Set M Day 7 (n = 4) | Set M Day 14 (n = 5) |
|---|---|---|---|
| No Wash Average | 782,458 | 750,544 | 750,156 |
| No Wash STDEV | +/−16,528 | +/−27,419 | +/−15,863 |
| No Wash Neg. Control Average | 11 | 14 | 70 |
| No Wash Neg. Control STDEV | +/−2 | +/−1 | +/−27 |
| Cycle I Average | 3,461 | 707 | 1,299 |
| Cycle I STDEV | +/−5,002 | +/−166 | +/−1,430 |
| Cycle I Neg. Control Average | 164 | 100 | 78 |
| Cycle I Neg. Control STDEV | +/−189 | +/−31 | +/−32 |
| Cycle II Average | 45 | 60 | 45 |
| Cycle II STDEV | +/−5 | +/−20 | +/−12 |
| Cycle II Neg. Control Average | 15 | — | — |
| Cycle II Neg. Control STDEV | +/−8 | — | — |

Example 8

Measurement of ATP from Surface-Treated Test Elements with ATP Spiked Coatings after Hospital Wash Disinfection Cycles Monitoring devices were prepared as in Example 7, four coatings of Preparative Example 6a (CELVOL 443), and brushing with the acid brush, to create Set N. The concentration of the CELVOL 443 portion of Preparative Example 6a used for Set N was 9.7 wt. %. Set N was divided multiple sub-groups that were used to assess the wash disinfecting cycles of hospital grade commercial machines. Four different machines, all of which were GETINGE DISINFECTION DECOMATT 8666 WASHER-DISINFECTORS, were used to process 9 loads of instruments using two different wash disinfection cycles. The "P1" cycle represented a "normal" load of surgical instruments and a regular wash cycle. The "P2" cycle represented a heavy duty wash cycle and contained surgical instruments that were typically more soiled than those in the "normal" load. The monitoring devices were placed in baskets with the surgical instruments and the baskets were placed into the washer disinfection machines in one of 4 locations: T=top rack, 2=second rack down, 3=third rack down, and B=bottom rack. Additionally, Negative Control test devices (untreated and uncoated) were run through the same cycles as Set N. After the wash disinfection cycles, the test devices were removed from the baskets and were then returned to their respective ATP test units and the amount of ATP on each test element was measured in a bioluminescent (i.e., luciferin/luciferase reaction) assay using a 3M CLEAN-TRACE NG Luminometer. Table 11 shows the ATP measurement results from Set N coated monitoring devices. Table 12 shows the ATP measurement results from the Negative Control test devices, processed with Set N.

TABLE 11

Set N - Amount of ATP detected from 4X coated test elements after Wash Disinfection Cycle in Hospital size Equipment. All results are reported in Average Relative Light Units (RLU).

| Load | Machine | Cycle | T | 2 | 3 | B |
|---|---|---|---|---|---|---|
| 1 | 4 | P1 | 731 | 2,404 | 3,786 | 474 |
| 2 | 2 | P1 | 28,456 | 2,764 | 4,342 | 2,200 |
| 3 | 1 | P2 | 3,618 | 3,393 | 3,670 | 2,393 |
| 4 | 4 | P2 | 338 | 2,816 | 5,494 | 2,776 |
| 5 | 2 | P2 | 2,822 | 3,287 | 1,768 | 306 |
| 6 | 3 | P2 | 11,484 | 8,196 | 6,609 | 6,053 |
| 7 | 1 | P2 | 2,591 | 2,723 | 2,512 | 2,080 |
| 8 | 3 | P2 | 3,032 | 3,247 | 4,775 | 4,154 |
| 9 | 1 | P1 | 8,160 | 1,441 | 1,330 | 1,594 |
| Average | — | — | | 6,804 | 3,363 | 3,698 | 2,448 |
| STDEV | — | — | +/−8,869 | +/−1,906 | +/−1,771 | +/−1,783 |

TABLE 12

Amount of ATP detected from Negative Control test devices after Wash Disinfection Cycle in Hospital size Equipment. All results are reported in Average Relative Light Units (RLU).

| Load | Machine | Cycle | T | 2 | 3 | B |
|---|---|---|---|---|---|---|
| 1 | 4 | P1 | 17 | 17 | 30 | 73 |
| 2 | 2 | P1 | 50 | 75 | 54 | 169 |
| 3 | 1 | P2 | 45 | 57 | 13 | 15 |
| 4 | 4 | P2 | 23 | 39 | 132 | 18 |
| 5 | 2 | P2 | 43 | 305 | 58 | 65 |
| 6 | 3 | P2 | 83 | 63 | 142 | 66 |
| 7 | 1 | P2 | 37 | 28 | 87 | 119 |
| 8 | 3 | P2 | 63 | 130 | 124 | 116 |
| 9 | 1 | P1 | 46 | 20 | 45 | 36 |
| Average | — | — | | 45 | 82 | 76 | 75 |
| STDEV | — | — | +/−20 | +/−91 | +/−41 | +/−51 |

Example 9

Measurement of ATP from Surface-Treated Test Elements with ATP Spiked Coatings after Wash Disinfection Cycle Three different test devices were coated with the Preparative Example 6a (CELVOL 443) according to the following procedures. Set 0 test devices were created by taking 3M CLEAN-TRACE SURFACE PROTEIN HIGH SENSITIVITY swab Cat# MPRO50, available from 3M Company of St. Paul, Minn., and pipetting onto it 0.2 mL of 0.7 micrograms/mL of ATP in a 9.7 wt. % CELVOL binder, otherwise prepared according to Preparative Example 6 and dried for 1 hour at 60° C. Set P test devices were created by taking 3M CLEAN-TRACE SURFACE ATP swab Cat# UXL100 (a rayon material swab), available from 3M Company, and pipetting onto it 0.2 mL of 0.7 micrograms/mL of ATP in a 9.7 wt. % CELVOL binder, otherwise prepared according to Preparative Example 6a and dried for 1 hour at 60° C. Set Q test devices were created by taking 3M CLEAN-TRACE SURFACE ATP swab Cat# UXL100, available from 3M Company, removing the swab tip (leaving only the "stick" portion of the device) and dip coating four times approximately 1.3 cm of the end of the stick with Preparative Example 6a solution containing 0.7 micrograms/mL of ATP in a 9.7 wt. % CELVOL binder and dried for 1 hour at 60° C. Each of Set O, P and Q were divided into 3 sub-groups. The 3 sub-groups were subjected to one of (1) "No Wash" or (2) the defective wash cycle "Incomplete Cycle I" described in Table 4, or (3) the nondefective wash cycle, "Complete Cycle II" described in Table 6. The test devices that were to be subjected to wash cycles were placed loosely in the corner of the stainless steel wire mesh baskets and processed the in a GETINGE 46-4 model washer disinfector described in Example 4. Afterwards the test devices were then to returned to their respective ATP test units and the amount of ATP on each test element was measured in a bioluminescent (i.e., luciferin/luciferase reaction) assay using a 3M CLEAN-TRACE NG Luminometer. Table 13 shows the ATP measurement results of Sets O, P and Q.

TABLE 13

Amount of ATP detected from coated test elements of various compositions. All results are reported in Relative Light Units (RLU).

| Conditions | Set O 9.7 wt. % CELVOL 433 MPRO50 swabs | Set P 9.7 wt. % CELVOL 433 UXL100 swabs | Set Q 9.7 wt. % CELVOL 433 Plain "sticks" |
|---|---|---|---|
| No Wash Average | 450,666 (n = 4) | 434,232 (n = 4) | 82,495 (n = 10) |
| No Wash STDEV | 27,433 | 18,468 | 12,392 |
| Cycle I Average | 5,137 (n = 5) | 3,745 (n = 5) | 19,963 (n = 8) |
| Cycle I STDEV | 2,261 | 2,929 | 19,796 |
| Cycle II Average | 433 (n = 5) | 425 (n = 4) | 7,518 (n = 10) |
| Cycle II STDEV | 200 | 126 | 9,467 |

Example 10

Measurement of ATP from Surface-Treated Test Elements with ATP Spiked Coatings after Hospital Wash Disinfection Cycles Monitoring devices were prepared as in Example 7, using four coatings of Preparative Example 6a (CELVOL 443) and brushing with the acid brush to create Set 1. The concentration of the CELVOL 443 portion of Preparative Example 6a used for Set 1 was 9.7 wt. %. Set 1 was divided multiple sub-groups that were used to assess the wash disinfecting cycles of hospital grade commercial machines. Two different machines, both of which were STERIS RELIANCE 444 WASHER DISINFECTOR, were used to process 9 loads of instruments using two different wash disinfection cycles. The "Instrument" cycle represented a "normal" load of surgical instruments and a regular wash cycle. The monitoring devices were placed in baskets with the surgical instruments and the baskets were placed into the washer disinfection machines in one of 4 locations: T=top rack, 2=second rack down, 3=third rack down, and B=bottom rack. After the wash disinfection cycles, the test devices were removed from the baskets and were then returned to their respective ATP test units and the amount of ATP on each monitoring device test element was measured in a bioluminescent (i.e., luciferin/luciferase reaction) assay using a 3M CLEAN-TRACE NG Luminometer. Table 14 shows the ATP measurement results from Set 1 coated monitoring devices.

TABLE 14

Set 1 - Amount of ATP detected from quadruple-coated test elements after Wash Disinfection Cycle in Hospital size Equipment. All results are reported in Average Relative Light Units (RLU).

| Load | Machine | Cycle | T | 2 | 3 | B |
|---|---|---|---|---|---|---|
| 1 | 1 | Instrument | 1,604 | 1,081 | 334 | 600 |
| 2 | 1 | Instrument | 1,331 | 860 | 1,345 | 8,035 |
| 3 | 1 | Instrument | 820 | 302 | 1,254 | 1,244 |
| 4 | 2 | Instrument | 205 | 208 | 258 | 273 |
| 5 | 2 | Instrument | 9,374 | 386 | 273 | 351 |
| 6 | 2 | Instrument | 242 | 201 | 474 | 201 |
| Average | — | — | 2,263 | 506 | 656 | 1,784 |
| STDEV | — | — | ±3,529 | ±372 | ±504 | ±3,085 |

Table 15. Set 1—Mean and upper control limit determined for each washer disinfector machine. All results are reported in Average Relative Light Units (RLU). The upper control limit in this instance was calculated as the mean plus three standard deviations. The calculated mean and standard deviation are shown in Table 14.

TABLE 15

Set 1 - Mean and upper control limit determined for each washer disinfector machine. All results are reported in Average Relative Light Units (RLU).

| Machine | Cycle | Mean | Upper Control Limit (Mean + 3σ) |
|---|---|---|---|
| 1 | Instrument | 1,047 | 12,706 |
| 2 | Instrument | 268 | 681 |

A two-sample T-test of the data comparing Machine 1 to Machine 2 resulted in a P-value of <0.001.

TABLE 16

Materials for Examples 11-12.

| | |
|---|---|
| CM-111 | Amorphous magnesium silicate purchased from 3M Company, St. Paul, MN, as 3M Cosmetic Microspheres CM-111 |
| YM plate | yeast and mold detection plate, obtained from 3M Company, St. Paul, MN, under the trade designation 3M PETRIFILM YEAST AND MOLD PLATE |
| YPD agar plate | agar plate prepared according to manufacturer's instructions with 5 wt % Yeast Extract Peptone Dextrose and 1.5 wt % agar, both powders from BD (DIFCO), Sparks MD |
| DI water | deionized, filtered, 18 megaohm water, processed through Milli-Q Gradient System obtained from Millipore; Waltham, MA |
| Fiber 1 | 1 denier fibrillated polyethylene fibers, obtained from Minifibers, Inc., Johnson City, TN, under the trade designation FYBREL600 |
| Fiber 2 | 6 denier 2 inches long chopped nylon fibers, obtained from Minifibers, Inc. |
| Fiber 3 | 1 denier bicomponent ethylene vinyl acetate/polypropylene fibers, obtained from Minifibers, Inc. |
| Fiber 4 | long glass fibers, obtained from Schuller, Inc., Denver, CO, under the trade designation MICRO-STRAND 106-475 GLASS MICROFIBERS |
| Flocculant | flocculant agent obtained from Midsouth Chemical Co., Inc., Ringgold, LA, under the trade designation 9307 FLOCCULANT |
| Latex binder | 50% solids vinyl acetate emulsion, obtained from Air Products Polymers, Allentown, PA, under the trade designation AIRFLEX 600BP |
| *Saccharomyces cerevisiae* ATCC 201390 | Purchased from American Type Culture Collection, Manassas, VA |
| Detergents used | GETINGE Alkaline cleaner detergent, catalog number 61301605277 (40 mL/4 gallons); GETINGE Dual enzyme instrument detergent, catalogue number 61301605269 (40 mL/4 gallons) |

Example 11

Preparation of Carrier Material A

A fiber premix was prepared by mixing 67.50 grams of Fiber 1, 13.50 grams of Fiber 2, 10.13 grams of Fiber 3, and 7.87 grams of Fiber 4 with 4 liters of cold tap water in a 4 L blender (available from VWR, Radnor, Pa., under the trade designation WARING COMMERCIAL HEAVY DUTY BLENDER, MODEL 37BL84) at medium speed for 30 seconds. The mixture was examined for uniform dispersion of the fibers without nits or clumps, and blended further for 15 seconds on low speed to break up clumps. The fiber premix was added to a 10 liter stainless steel beaker and mixed with an impeller mixer (obtained from ThermoFisher Scientific, Waltham, Mass., under the trade designation STEDFAST STIRRER MODEL SL2400) at a speed setting of 4 for five minutes. Then 0.6 grams of latex binder was dispersed in about 25 mL of tap water in a 50 mL beaker and added to the mixture. The beaker was rinsed with about another 25 mL of tap water that was added to the mixture and mixed for about 2 minutes. An amount of 22.5 grams of CM-111 powder was added to the mixture and mixed for about 1 minute. In the same manner as latex binder, 0.6 grams of flocculant was dispersed in about 25 mL of tap water and added to the mixture while mixing, followed by the addition of about another 25 mL of rinse water from the beaker. The latex binder crashed out of solution onto the fibers and the liquid phase of the premix changed from cloudy to substantially clear.

A felt of the above material was prepared using a pad maker apparatus (obtained from Williams Apparatus, Watertown, N.Y., under the trade designation TAPPI). The pad maker had a box measuring about 30 centimeters (12 inches)

square and 30 centimeters (12 inches) high with a fine mesh screen at the bottom and a drain valve. The box was filled with tap water up to a height of about 1 centimeter above the screen. The mixture containing CM-111 was poured into the box and the valve was opened immediately which created a vacuum that pulled the water out of the box. The resulting wet-laid felt was approximately 3 millimeters thick. The wet-laid felt was transferred from the apparatus onto a 20 centimeter square sheet of blotter paper (96-pound white paper, obtained from Anchor Paper, St. Paul, Minn.). The felt was sandwiched between 2 to 4 layers of blotter paper, to blot excess water. The pressed felt was then transferred onto a fresh sheet of blotter paper and placed in an oven (obtained from SPX Thermal Product Solutions, White Deer, Pa., under the trade designation BLUE M STABIL-THERM OVEN, MODEL OV-560A2) set at 110° C. for about 2 hours to remove residual water and cure the latex binder to form a porous matrix.

Example 12

Preparation of Carrier Material B

Example 12 was another fiber premix and felt prepared according to the procedure described for Example 11, above, except that the fiber premix contained 25 grams of Fiber 1, 5.06 grams of Fiber 2, 3.80 grams of Fiber 3, and 2.95 grams of Fiber 4 and the amount of CM-111 was 8.44 g to form carrier material B.

Preparation of Yeast Stock Solution

A single isolated colony from a streak culture of *Saccharomyces cerevisiae* (*S. cerevisiae*) from a YPD agar plate was used to inoculate 5 mL yeast extract potato dextrose broth (YPD Broth prepared 5% w/v, purchased from Becton Dickenson, Sparks, Md.) and incubated overnight at 30° C.

Spiking Carrier Material A and B with Yeast

Several 6 mm diameter disks, were die-punch cut from the carrier material A (Example 11) and carrier material B (Example 12), described above. A 100 microliter volume from the overnight yeast stock solution, containing approximately $1 \times 10^8$ CFU/mL, was added on top of each of the sample disks of Example 11 and Example 12. The resulting yeast spiked disks of Example 11 and Example 12 contained approximately $1.8 \times 10^7$ CFUs/mL of *S cerevisiae* (based on colony counts on YM Plate), and were stored in a sterile petri dish at room temperature (about 25° C.) overnight.

Mounting Yeast Spiked Disks of Example 11 and Example 12

Disks of Example 11 and Example 12, all spiked with yeast, were mounted into one of two different types of monitoring devices. Monitoring device #1 was created by utilizing the plastic box and rack used in the packaging of disposable pipet tips. The plastic box with a 96-hole rack (8×12 holes) for sterile disposable auto-pipet tips, available from VWR International as catalog number 82003-196, STERILE AEROSOL PIPET TIPS 96 TIP RACKS, was opened and emptied of the disposable pipet tips. The 96-hole rack was removed from the sleeve holder and set aside. Sample disks of Example 11 and Example 12 (spiked with yeast) were placed on the sleeve holder. The sleeve holder also contained holes which matched the holes in the rack for holding pipet tips. The 96-hole rack was then replaced over the samples, thus securing them between the sleeve holder and the rack. This arrangement still exposing most of both sides of the sample disks to the holes in the rack and sleeve holder. The open side of the sleeve holder was closed by taping the cover of onto the sides of the sleeve holder.

Monitoring device #2 was created by positioning the sample disks of Example 11 and Example 12 between two stainless steel plates, held in place with typical office supply type paper binder clips. The stainless steel plates each contained an array of 6×6 machined holes of about 4 mm in diameter. The disks of Example 11 and Example 12 were positioned such that they were held in place by the two stainless steel plates of Monitoring Device #2 but the majority of the disks were still exposed on both sides. Both Monitoring device #1 and Monitoring device #2 allowed the free flow of water and detergent over the sample disks, during the washer disinfection cycle.

Washer Disinfector Cycle

The yeast spiked disks of Example 11 and Example 12, mounted on Monitoring device #1 and Monitoring device #2 were placed the GETINGE 46-4 model-washer disinfector (Getinge USA, Inc., Rochester, N.Y.) and subjected to the INSTRM-LONG-D-3 cycle, a cycle which is commonly used in hospitals. The optional step of adding "lubricant/instrument milk" during mid cycle was omitted. The washer cycle had both enzymatic detergent and alkaline detergent as indicated in Table 17, which shows the steps in the INSTRM-LONG-D-3 wash cycle.

TABLE 17

INSTRM-LONG-D-3 cycle

| Step | Program phase | Water | Injections | Time[1] |
|---|---|---|---|---|
| 1 | Pre-rinse | Cold water | n/a | 3 minutes |
| 2 | Wash - 1 | Hot water | 60 mL Enzyme detergent | 7 minutes |
| 3 | Wash - 2 | Hot water | 60 mL Alkaline detergent | 9 minutes |
| 4 | Post-rinse 1 | Hot water | n/a | 3 minutes |
| 5 | Post rinse 2 | Hot water | n/a | 3 minutes |
| 6 | Final rinse | Hot water | n/a | 10 minutes |
| 7 | Drying | No water | n/a | 12 minutes |

[1]All times are approximate and include the equilibration period needed for the washer to reach the prescribed temperature.

Measurement of ATP from Yeast Spiked CM-111 Carrier Material after Wash Disinfection Cycle.

After processing the yeast-spiked disks in the INSTRM-LONG-D-3 washing cycle, the disks of Example 11 and Example 12 were removed from Monitoring device #1 and Monitoring device #2 and were temporarily transferred to sterile petri dishes. The disks were then transferred into empty sterile 1.5 mL polypropylene micro-centrifuge tubes (VWR, Catalog #89000-028). Each of the sample disks were prepared for ATP analysis by adding 100 microliters of an extractant solution and 500 microliters of an enzyme solution from a sample preparation kit (obtained from 3M Company; St. Paul, Minn., under the trade designation 3M CLEAN-TRACE SURFACE ATP SYSTEM) to the tube containing the disks. The contents were mixed for 5 seconds at about 3200 rpm on a vortex mixer (obtained from VWR, West Chester Pa., under the trade designation VWR FIXED SPEED VORTEX MIXER). The ATP signal of the sample was measured in relative light units (RLU) for one minute at 10 second intervals using a bench-top luminometer (obtained from Turner Biosystems, Sunnyvale, Calif., under the trade designation 20/20N SINGLE TUBE LUMINOMETER, equipped with 20/20n SIS software). Positive control samples were also created by preparing unwashed sample disks of Example 11 and Example 12 (spiked with yeast) for ATP analysis in the same fashion as described above. The luminescence values in RLU were converted to Log base 10 ($\log_{10}$) and are reported in Table 18, below. The $\log_{10}$ Reduction Value (LRV) was also calculated by subtracting the $Log_{10}$ RLU value of the washed disks from the $Log_{10}$ RLU value of the respective positive control (unwashed disks). All Example results in Table 18 were the average of duplicate disks. Each average value had a relative variance of less than 10%, with the one exception of Example 11 on Monitoring device #1, which had a relative variance of 20%. Table 18 demonstrates that a living microorganism such as yeast can be adhered to a carrier and subjected to a wash disinfection cycle to assess the effectiveness of the wash disinfection cycle by measuring the residual amount of ATP.

TABLE 18

Amount of ATP detected from Yeast Spiked Examples 11 and 12. All results are reported in $Log_{10}$ Relative Light Units (RLU).

| Sample | ATP Signal ($Log_{10}$ RLU) | LRV |
| --- | --- | --- |
| Example 11 Unwashed (positive control) | 6.2 | — |
| Example 11 on Monitoring device #1 | 4.6 | 1.7 |
| Example 11 on Monitoring device #2 | 4.1 | 2.1 |
| Example 12 Unwashed (positive control) | 6.7 | — |
| Example 12 on Monitoring device #1 | 3.6 | 3.1 |
| Example 12 on Monitoring device #2 | 4.2 | 2.6 |

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims:

The invention claimed is:

1. A monitoring device, made by the following process:
depositing a test composition comprising a predetermined quantity of tracer analyte onto a test portion of a movable test element, the test element comprising a handle for grasping the test element;
depositing a detection reagent into a container, the container comprising a first end with an opening, a second end opposite the first end, and a frangible seal;
wherein a receiving chamber is disposed on a first side of the frangible seal proximate the opening and a cuvette chamber is disposed on a second side of the frangible seal distal the opening;
wherein the container is configured to receive the test portion and configured to be operationally coupled to an analytical instrument; and
wherein the test element is configured to be able to actuate the frangible seal;
positioning the test element relative to the container such that at least a portion of the test element extends through the opening into the container;
wherein at least a portion of the handle extends outside the container;
wherein the test element is configured to be able to actuate the frangible seal;
wherein the tracer analyte and the detection reagent each are capable of participating in one or more chemical reaction that results in the formation of a detectable product.

2. The monitoring device of claim 1, wherein the test portion comprises at least one recessed area, wherein the test composition is adhered in the recessed area.

3. The monitoring device of claim 1, further comprising a secural element configured to releasably hold the monitoring device at a fixed location within an automated washer.

4. The monitoring device of claim 3, wherein the secural element comprises one or more engagement structures configured to hold a portion of an automated washer rack or a wire basket.

5. The monitoring device of claim 1, wherein the predetermined quantity is a known quantity.

6. A system for testing the efficacy of a washing process, comprising:
a monitoring device comprising a test element that includes a test portion to which a test composition comprising a known quantity of a tracer analyte is releasably adhered according to claim 1; and
an analytical instrument capable of detecting the detectable product;
wherein the container is configured to receive the test portion and configured to be operationally coupled to the analytical instrument.

7. A method of assessing the efficacy of a washing process, comprising:
exposing the test portion of a monitoring device according to claim 1 to the washing process;
after exposing the test portion to the washing process, contacting the test portion with the detection reagent in the container; and
using the analytical instrument to detect a presence or an absence of the detectable product;
wherein the presence of the detectable product indicates a presence of tracer analyte on the test portion after exposing the test portion to the washing process.

8. The method of claim 7, wherein exposing the test portion to the washing process comprises placing the test portion into an automated washer and performing at least a portion of an automated wash cycle while the test portion is disposed in the automated washer.

9. The method of claim 7, wherein using the analytical instrument to detect a presence or an absence of the detectable product comprises using the analytical instrument to measure a quantity of the tracer analyte.

10. The method of claim 9, wherein exposing the test portion of a monitoring device comprises exposing the test portion of a plurality of monitoring devices, wherein the method further comprises positioning a first monitoring device at a first predefined location in the automated washer and positioning a second monitoring device at a second predefined location in the automated washer.

11. The method of claim 10, further comprising the step of comparing a measured quantity of tracer analyte associated with the first monitoring device to a measured quantity of tracer analyte associated with the second monitoring device.

12. The method of claim 9, further comprising comparing at least one measured quantity of the tracer analyte to a predefined standard.

13. The method of claim 7, further comprising the step of placing the test portion of the monitoring device in a receiver configured to restrict fluidic accessibility to the test portion.

14. The method of claim 7 further comprising, before exposing the test portion of the monitoring device to the washing process, positioning at least a part of the test portion of the monitoring device in a process challenge device.

15. A method of processing an object to be decontaminated, comprising:
processing as a single batch in a decontamination process:
an object having an unknown amount of biological soil disposed thereon and/or therein;
a monitoring device comprising a predetermined quantity of tracer analyte according to claim 1;
after exposing the test portion to the decontamination process, contacting the test portion with the detection reagent in the container; and
using the analytical instrument to detect a presence or an absence of the detectable product;
wherein the presence of the detectable product indicates a presence of the tracer analyte on the test portion after exposing the test portion to the washing process.

16. The method of claim 15, wherein processing the object and the monitoring device in a decontamination process comprises processing the object and the monitoring device in an automated washer or an automated washer-disinfector.

17. The method of claim 15, wherein processing as a single batch in a decontamination process the object and the monitoring device comprises processing as a single batch in a decontamination process the object and a plurality of the monitoring devices.

18. The method of claim 15, wherein detecting a presence or an absence of the detectable product further comprises calculating a quantity of tracer analyte remaining on the test portion after exposing the test portion to the decontamination process.

19. The method of claim 18, further comprising comparing the quantity of tracer analyte remaining on the test portion of at least one monitoring device after exposing the test portion to the decontamination process to a predetermined quantity of tracer analyte associated with an action limit.

20. The method of claim 19, further comprising i) releasing the object for use in a first subsequent process if the quantity of tracer analyte remaining on the test portion of the at least one monitoring device after exposing the test portion to the decontamination process is less than or equal to the predetermined quantity or ii) releasing the object for use in a second subsequent process if the quantity of tracer analyte remaining on the test portion of the at least one monitoring device after exposing the test portion to the decontamination process is greater than or equal to the predetermined quantity.

21. A kit, comprising:
a container comprising a first end with an opening, a second end opposite the first end, and a frangible seal, wherein a receiving chamber is disposed on a first side of the frangible seal proximate the opening and a cuvette chamber is disposed on a second side of the frangible seal distal the opening, and wherein the container includes a detection reagent disposed therein; and
a movable test element made by a process of releasably depositing a test composition comprising a predetermined quantity of tracer analyte onto a test portion of the test element; wherein the test element comprises a handle for grasping the test element
wherein the container is configured to receive the test portion and configured to be operationally coupled to an analytical instrument;
wherein the tracer analyte and the detection reagent each are capable of participating in one or more chemical reaction that results in the formation of a detectable product.

* * * * *